US008344327B2

(12) United States Patent
Yamaguchi

(10) Patent No.: US 8,344,327 B2
(45) Date of Patent: Jan. 1, 2013

(54) RADIATION IMAGE DETECTOR TIME DEPENDENT DEGRADATION DETERMINATION METHOD AND APPARATUS

(75) Inventor: Yoshitaka Yamaguchi, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 298 days.

(21) Appl. No.: 12/923,026

(22) Filed: Aug. 30, 2010

(65) Prior Publication Data

US 2011/0049343 A1 Mar. 3, 2011

(30) Foreign Application Priority Data

Aug. 31, 2009 (JP) .................................. 2009-200424

(51) Int. Cl.
*G01T 1/166* (2006.01)

(52) U.S. Cl. ................................................. 250/363.07

(58) Field of Classification Search ............. 250/363.01, 250/363.02, 363.07, 363.09, 370.01, 370.08, 250/371; 378/98.8; 382/132
See application file for complete search history.

(56) References Cited

FOREIGN PATENT DOCUMENTS

| JP | 11-244270 | 9/1999 |
|----|-----------|--------|
| JP | 2006-156555 | 6/2006 |

OTHER PUBLICATIONS

Fuzio Yamaguchi "Graphic Processing Engineering Through Computer Graphic Display" The Nikkan Kogyo Shimbun, Ltd., pp. 73-75; 1981.

*Primary Examiner* — Mark R Gaworecki
(74) *Attorney, Agent, or Firm* — Jean C. Edwards, Esq.; Edwards Neils PLLC

(57) ABSTRACT

Clearly notifying that a setting error of an imaging plane of a radiation image detector is on the increase. For a radiation image detector having an imaging plane with pixels, disposed in a two-dimensional matrix, for storing charges by receiving radiation according to an amount of radiation received and used to receive radiation transmitted through the same subject each time the detector is shifted and changed in position along a predetermined shift axis, a setting error of the imaging plane, i.e., an inclination of the two-dimensional matrix with respect to the shift axis or the like is detected a plurality of times with the passage of time and, when a fluctuation range of a plurality of setting errors so detected exceeds a predetermined acceptable range, an indication or an alarm so indicating is given.

17 Claims, 13 Drawing Sheets

RADIATION FIELD CENTER    RADIATION FIELD CENTER

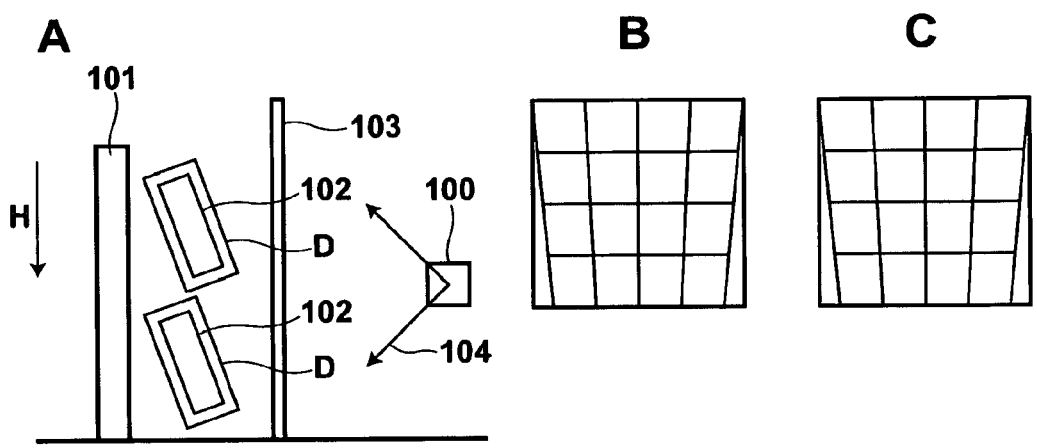
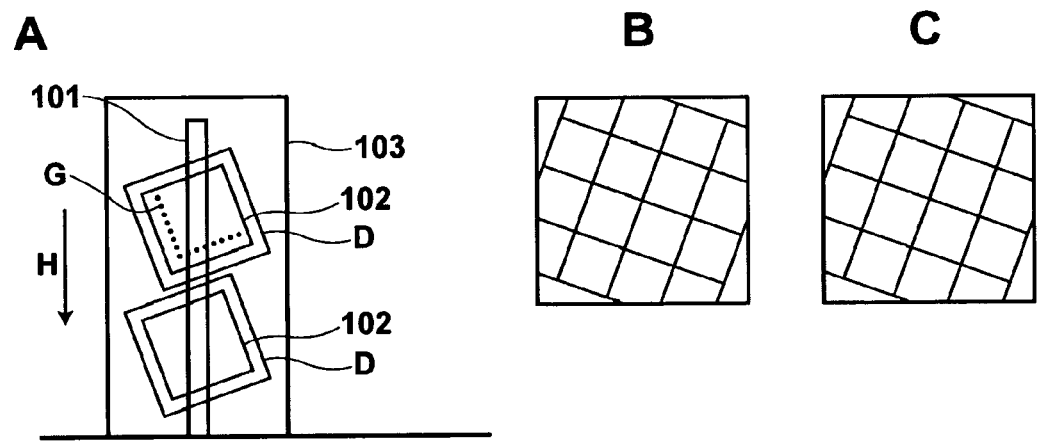

FIG.14
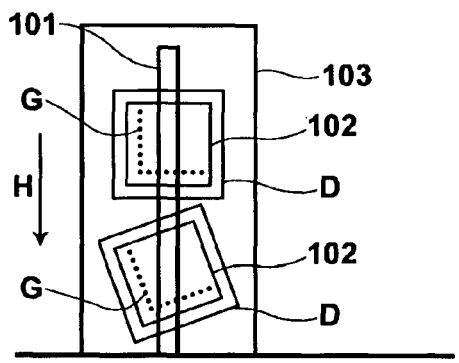
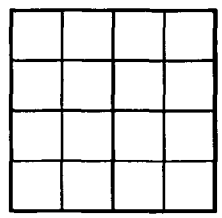
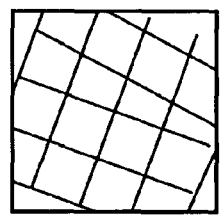
A  B  C
FIG.15
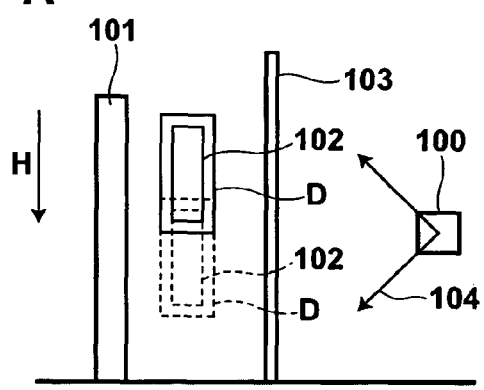
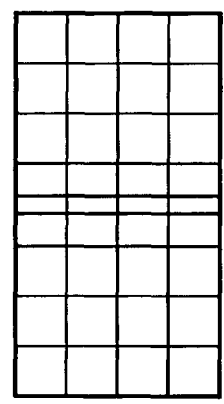
A  B  C
FIG.16
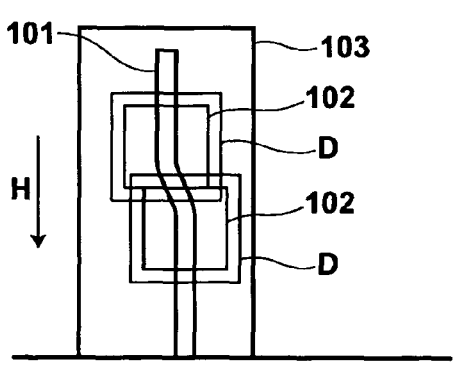
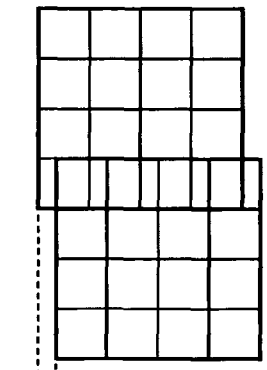
A  B  C

RADIATION IMAGE DETECTOR TIME DEPENDENT DEGRADATION DETERMINATION METHOD AND APPARATUS

CROSS-REFERENCE TO RELATED APPLICATIONS

The present application claims priority from Japanese Patent Application No. 2009-200424, filed Aug. 31, 2009, the contents of which are herein incorporated by reference in their entirety.

BACKGROUND OF THE INVENTION

1. Field of the Invention

The present invention relates to a time dependent degradation determination method for a radiation image detector and, more particularly, to a method of determining whether or not a setting error of an imaging plane of the radiation image detector is on the increase, and an apparatus for implementing the method.

2. Description of the Related Art

Panel type radiation image detectors are put into practical use. Such a detector includes an imaging plane having pixels, each storing charges by receiving radiation representing image information according to an amount of radiation received, disposed in a two-dimensional matrix and outputs image data representing the image information through a reading operation, as described, for example, in Japanese Unexamined Patent Publication No. 2006-156555. Generally, the pixels include a charge generation layer that generates charges by receiving radiation, a voltage application electrode for applying a voltage to the charge generation layer, a charge collection electrode for collecting the charges generated in the charge generation layer, and a switching element for reading out the charges collected by the charge collection electrode, which are formed, for example, of a TFT (thin film transistor) active matrix array.

Generally, the panel type radiation detectors described above are formed in a quadrangle, i.e., a rectangle or a square, and used widely to record transmitted radiation image information of a subject by emitting radiation transmitted through the subject. The quadrangularly shaped radiation image detector may sometimes be used for recording a long length image representing a long portion of a subject, such as the entire spine of a human body, in which the detector is shifted along a predetermined shift axis and receives radiation transmitted through the same subject at each shifted position.

When the panel type radiation detector is used in the manner as described above, a reading operation is performed with respect to each emission of radiation (radiation image recording) and image data representing a radiation image are obtained by each reading operation. Thereafter, these image data are combined together to obtain image data representing a long portion of a subject. As for the method of obtaining image data representing a long length radiation image in the manner as described above, for example, Japanese Unexamined Patent Publication No. 11 (1999)-244270 describes a method that uses, as an example, a cassette having a phosphor screen.

In the mean time, when combining radiation images in the manner as described above, a misalignment may sometimes occur at a joint of the combined image due to an inclination of the imaging plane of the panel type radiation image detector.

There are several types of "inclination of imaging plane", which will be described, hereinafter, in detail with reference to FIGS. 10 and 11.

A of FIG. 10 schematically illustrates a system for recording (imaging) a radiation image viewed from a side thereof. In the drawing, reference numeral 100 is a radiation source, reference numeral 101 is a stand for guiding a panel type quadrangular radiation image detector D, and the reference numeral 102 is the imaging plane of the radiation image detector D. In this example, it is assumed that grid 103 will be recorded as the subject in order to facilitate understanding of the problem. That is, imaging plane 102 of the radiation image detector D will be exposed by radiation 104 emitted from radiation source 100 and transmitted through grid 103.

In this case, the panel type quadrangular radiation image detector D is set such that the panel surface and one side of the panel become parallel to a direction in which stand 101 extends (arrow H direction) and shifted in the arrow H direction. That is, the arrow H direction is the shift axis in this case. The radiation image detector D, standing still before and after the shifting, is exposed to radiation 104 transmitted through grid 103, whereby first and second operations of radiation image taking are performed.

Here, one problem may arise that imaging plane 102 (two-dimensional pixel matrix constituting the imaging plane) is inclined by an angle of $\alpha$ with respect to the panel surface due to an assembly error of the radiation image detector D or the like and, if so, radiation images of grid 103 obtained by the first and second radiation emissions become like that shown in B and C of FIG. 10 respectively. That is, when joining a lower edge portion of first recorded image with an upper edge portion of second recorded image, the horizontal length of the subject differs between these portions and misalignment occurs at the joint.

In this case, the inclination angle $\alpha$ of the radiation image detector D with respect to the panel surface corresponds to the inclination angle thereof with respect to the shift axis H of the two-dimensional matrix since the radiation image detector D is set in the manner as described above.

Next, another problem will be described with reference to FIG. 11. A of FIG. 11 schematically illustrates a system for recording (imaging) a radiation image viewed from the front. In the drawing, reference numerals 101, 102, 103 are a stand, an imaging plane, and a grid respectively which are identical to those shown in A of FIG. 10. In this case, the radiation source is omitted in the drawing, but disposed such that radiation is emitted along an emission axis perpendicular to the plane of the drawing.

Also, in this case, the panel type quadrangular radiation image detector D is set in the same manner as in A of FIG. 10 and shifted in the arrow H direction, in which the radiation image detector D, standing still before and after the shifting, is exposed to radiation, whereby first and second operations of radiation image taking are performed.

Here, as another problem, two-dimensional pixel matrix may sometimes be inclined by an angle of $\gamma$ with respect to one side of the panel in a plane parallel to the panel surface (plane parallel to the plane of the drawing) due to an assembly error of the radiation image detector D or the like. Note that some of the pixels are denoted by G in A of FIG. 11. If that is the case, radiation images of grid 103 obtained by the first and second radiation emissions become like that shown in B and C of FIG. 11 respectively. That is, when joining a lower edge portion of first recorded image with an upper edge portion of second recorded image, a fault slip like misalignment occurs at the joint.

In this case also, the inclination angle γ of the two-dimensional matrix with respect to one side of the panel corresponds to the inclination angle thereof with respect to the shift axis H of the two-dimensional matrix since the radiation image detector D is set in the manner as described above.

Taking the case, as an example, in which the size of the radiation image detector D is 40 cm×40 cm, the distance (SID) from the radiation source to the imaging plane is 180 cm, the misalignment at the joint of the combined image is about 0.5 mm when the inclination angle α is 0.31° or when inclination angle γ is 0.07°, which is significantly large.

So far, the problems of the case in which the panel type quadrangular radiation image detector is shifted accurately along the shift axis parallel to the surface and one side of the detector, and the two-dimensional matrix of pixels is inclined in the detector have been described. But, even in the case where the two-dimensional pixel matrix is not inclined in the radiation image detector, that is, the matrix is formed parallel to the surface and one side of the panel type quadrangular radiation image detector, if the radiation image detector itself is disposed inclined with respect to the detector shift axis, then the problems similar to those described above will naturally occur. Statuses when the radiation image detector itself is inclined in this way and the two-dimensional matrix is inclined with respect to detector shift axis by inclination angles α, γ are shown in FIGS. 12 and 13 respectively.

Here, the description has been made of a case in which the inclination of the matrix is constant even the radiation image detector is shifted. Where the radiation image detector is gradually inclined as it is shifted, the inclination of the matrix varies with the shifting of the radiation image detector. In such a case, a similar problem will occur. FIG. 14 schematically illustrates such situation, in which A of FIG. 14 schematically illustrates a system for recording (imaging) a radiation image viewed from the front. In the drawing, reference numerals 101, 102, 103 are a stand, an imaging plane, and a grid respectively which are identical to those shown in A of FIG. 10. Also in this case, the radiation source is omitted in the drawing, but disposed such that radiation is emitted along an emission axis perpendicular to the plane of the drawing.

In this case, a matrix inclination occurs as the radiation image detector is shifted and at the same time the matrix is shifted in a lateral direction. Such a phenomenon occurs due to, for example, low accuracy of a guide mechanism for guiding the movement of the radiation image detector, setting of a relatively large gap between, for example, a guide rod and a guide member of the guide mechanism, or the like.

At this time, radiation images of grid 103 obtained by the first and second radiation emissions become like that shown in B and C of FIG. 14 respectively. Also in this case, when joining a lower edge portion of first recorded image with an upper edge portion of second recorded image, a fault slip like misalignment occurs at the joint.

Further, the problem of misalignment at an image joint also occurs not only when the pixel matrix is inclined but also when the matrix is displaced from a predetermined position at the time of radiation emission. Hereinafter, the displacement will be described in detail.

FIG. 15 schematically illustrates the situation when such displacement occurred. A of FIG. 15 schematically illustrates a system for recording (imaging) a radiation image viewed from a side thereof. In the drawing, reference numeral 100 denotes a radiation source. Normally, when taking radiation images to be combined, the radiation image detector D is placed at positions at the time of first and second radiation emissions so as to overlap to a certain extent in the direction of shift axis H. For example, if aging deterioration has occurred in the moving mechanism of the radiation image detector D, however, the radiation image detector D may be displaced in a direction parallel to shift axis H from the predetermined position at each radiation emission. FIG. 15 illustrates an example case in which the radiation image detector D is displaced downward from the predetermined position by a length Δy at the second radiation emission.

At this time, radiation images of grid 103 obtained by the first and second radiation emissions become like that shown in B and C of FIG. 15 respectively. In this case, image combining is performed as the position in the first recorded image denoted by $y_0$ in B of FIG. 15 would be matched with the upper edge of the second recorded image. In actuality, however, the upper edge of the second recorded image is displaced by the length Δy and, therefore, misalignment occurs at the image joint.

Further, such displacement as described above may sometimes occur in a direction orthogonal to shift axis H, as well as in a direction parallel to shift axis H. FIG. 16 schematically illustrates a situation in which such displacement has occurred. A of FIG. 16 schematically illustrates a system for recording (imaging) a radiation image viewed from the front. The radiation source is omitted in the drawing, but disposed such that radiation is emitted along an emission axis perpendicular to the plane of the drawing.

Normally, when taking radiation images to be combined, the radiation image detector D is placed at positions corresponding to each other in a direction orthogonal to shift axis H at the time of first and second radiation emissions. For example, if aging deterioration has occurred in the moving mechanism of the radiation image detector D or if stand 101 (more specifically, the rail for guiding the radiation image detector D) is curved as shown in the drawing, however, the radiation image detector D may be displaced in a direction orthogonal to shift axis H from the predetermined position at the time of radiation emission. FIG. 16 illustrates an example case in which the radiation image detector D is displaced to the right side from the predetermined position by a length Δx at the second radiation emission.

At this time, radiation images of grid 103 obtained by the first and second radiation emissions become like that shown in B and C of FIG. 16 respectively. In this case, image combining is performed as the positions of the first and second recorded images in the left/right direction, i.e., in a direction orthogonal to shift axis H would correspond to each other. In actuality, however, the second recorded image is displaced by the length Δx and, therefore, misalignment occurs at the image joint.

Aforementioned Japanese Unexamined Patent Publication No. 11 (1999)-244270 also describes a method which, when combining two images in the manner as described above, takes images of a grid provided in the cassette together with images of a subject and corrects the misalignment between the two images (in this case, the misalignment arising from the difference in distance between the subject and imaging plane) based on the grid images. But the method described in Japanese Unexamined Patent Publication No. 11 (1999)-244270 can not detect the inclination or displacement of the two-dimensional matrix that will occur when a panel type quadrangular radiation image detector is used. Therefore, it is obvious that the method can not correct misalignment between images based on such inclination or displacement.

Consequently, it is conceivable to detect the inclination or displacement of the two-dimensional matrix, which is a setting error of the imaging plane of a radiation image detector, and to perform correction processing on the two images to be combined for eliminating distortion based on the detected inclination or displacement. The inclination or displacement of the two-dimensional matrix, however, may increase due to aging deterioration, so that continued performance of the correction processing under the same condition without knowing this causes a problem that a misalignment occurs in an image joint even after the correction processing has been performed.

The present invention has been developed in view of the circumstances described above and it is an object of the present invention to provide a time dependent degradation determination method for a radiation image detector capable of clearly notifying a user that a setting error of the imaging plane of a radiation image detector has increased to an extent that exceeds an acceptable range.

It is a further object of the present invention to provide a time dependent degradation determination apparatus for a radiation image detector capable of implementing the time dependent degradation determination method for a radiation image detector described above.

SUMMARY OF THE INVENTION

A first time dependent degradation determination method for a radiation image detector of the present invention is a method for a radiation image detector which includes an imaging plane for storing charges by receiving radiation transmitted through a subject according to an amount of radiation received and outputs image data representing radiation image information of the subject through a reading operation, the detector being used to receive radiation transmitted through the same subject each time the detector is shifted and changed in position along a predetermined shift axis, the method including the steps of:

detecting a setting error of the imaging plane a plurality of times with the passage of time; and providing, when a fluctuation range of a plurality of setting errors detected exceeds a predetermined acceptable range, an indication or an alarm so indicating.

A second time dependent degradation determination method for a radiation image detector of the present invention is a method for a radiation image detector which includes an imaging plane for storing charges by receiving radiation transmitted through a subject according to an amount of radiation received and outputs image data representing radiation image information of the subject through a reading operation, the detector being used to receive radiation transmitted through the same subject each time the detector is shifted and changed in position along a predetermined shift axis, the method including the steps of:

detecting a setting error of the imaging plane a plurality of times with the passage of time; and providing, when a difference between a setting error detected first and at least one another setting error subsequently detected exceeds a predetermined acceptable difference, an indication or an alarm so indicating.

Preferably, when the radiation image detector is a radiation image detector having an imaging plane with pixels for storing charges disposed in a two-dimensional matrix, an inclination of the matrix with respect to the shift axis is detected as the setting error.

In order to detect such an inclination of the matrix, it is preferable that radiation is emitted to the radiation image detector two times by changing the position of the radiation image detector by the shifting so that a common marker is imaged by each radiation emission, image data representing radiation image information of the marker are obtained by performing the reading operation after each radiation emission, and the inclination is detected based on a positional relationship between each image of the marker represented by image data obtained by each reading operation.

Preferably, the inclination to be detected described above is an inclination in a plane that includes each radiation emission axis in each radiation emission. Alternatively, the inclination may be an inclination in a plane which is orthogonal to a plane that includes each radiation emission axis in each radiation emission and which includes the shift axis.

When the radiation image detector is a radiation image detector having an imaging plane with pixels for storing charges disposed in a two-dimensional matrix, a displacement of the matrix from a predetermined position when receiving radiation may be detected as the setting error.

In order to detect such a displacement of the matrix, it is preferable that radiation is emitted to the radiation image detector two times by changing the position of the radiation image detector by the shifting so that a common marker is imaged by each radiation emission, image data representing radiation image information of the marker are obtained by performing the reading operation after each radiation emission, and the displacement is detected based on a positional relationship between each image of the marker represented by image data obtained by each reading operation.

The displacement may be a displacement in a direction orthogonal or parallel to the shift axis.

In the time dependent degradation determination method for a radiation image detector according to the present invention, it is preferable that, when combining image data outputted from the radiation image detector that received radiation transmitted through the same subject each time the detector was shifted and changed in position along the predetermined shift axis, the image data representing the subject with respect to each position, correction processing for eliminating an image distortion arising from the setting error is performed on at least a portion of the image data prior to combining the image data, while the correction processing is not performed if a situation arises in which the indication or the alarm needs to be provided.

A first time dependent degradation determination apparatus for a radiation image detector of the present invention is an apparatus for implementing the first time dependent degradation determination method for a radiation image detector described above, the apparatus including:

a means for detecting a setting error of the imaging plane a plurality of times with the passage of time;

a means for storing a plurality of setting errors detected; and a means for providing, when a fluctuation range of a plurality of setting errors stored exeeds a predetermined acceptable range, an indication or an alarm so indicating.

A second time dependent degradation determination apparatus for a radiation image detector of the present invention is an apparatus for implementing the second time dependent degradation determination method for a radiation image detector described above, the apparatus including:

a means for detecting a setting error of the imaging plane a plurality of times with the passage of time;

a means for storing a plurality of setting errors detected; and a means for providing, when a difference between a setting error detected first of a plurality of setting errors stored and at least one another setting error subsequently detected exceeds a predetermined acceptable difference, an indication or an alarm so indicating.

A time dependent degradation determination apparatus for a radiation image detector according to a preferred embodiment of the present invention is an apparatus for detecting the inclination based on the marker images described above, the apparatus including:

a radiation emission means for emitting radiation, through the common marker, to the radiation image detector;

a shifting means for shifting the radiation image detector in the shift axis direction;

a means for obtaining image data from the radiation image detector each time the shifting and radiation emission are performed; and a calculation means for calculating the inclination based on a positional relationship between each image of the marker represented by the image data obtained.

A time dependent degradation determination apparatus for a radiation image detector according to another preferred embodiment of the present invention is an apparatus for detecting the displacement based on the marker images described above, the apparatus including:

a radiation emission means for emitting radiation, through the common marker, to the radiation image detector;

a shifting means for shifting the radiation image detector in the shift axis direction;

a means for obtaining image data from the radiation image detector each time the shifting and radiation emission are performed; and a calculation means for calculating the displacement based on a positional relationship between each image of the marker represented by the image data obtained.

In the first time dependent degradation determination method for a radiation image detector of the present invention, when a setting error of the imaging plane is detected a plurality of times with the passage of time, if a fluctuation range of a plurality of setting errors detected exceeds a predetermined acceptable range, it is thought that the setting error has increased significantly in comparison with the beginning. Therefore, if such is the case, provision of an indication or an alarm may clearly notify the user that the time dependent degradation of the radiation image detector has progressed to an extent that exceeds an acceptable range.

In the second time dependent degradation determination method for a radiation image detector of the present invention, when a setting error of the imaging plane is detected a plurality of times with the passage of time, if a difference between a setting error detected first and at least one another setting error subsequently detected exceeds a predetermined acceptable difference, it is also thought that the setting error has increased significantly in comparison with the beginning. Therefore, if such is the case, provision of an indication or an alarm may clearly notify the user that the time dependent degradation of the radiation image detector has progressed to an extent that exceeds an acceptable range.

In the time dependent degradation determination method for a radiation image detector of the present invention, in order to detect, in particular, the inclination or displacement of the pixel matrix of the imaging plane of the radiation image detector, if radiation is emitted to the radiation image detector two times by changing the position of the radiation image detector by the shifting so that a common marker is imaged by each radiation emission, image data representing radiation image information of the marker are obtained by performing the reading operation after each radiation emission, and the inclination or displacement is detected based on a positional relationship between each image of the marker represented by image data obtained by each reading operation, the inclination or the displacement may be detected accurately.

In the time dependent degradation determination method for a radiation image detector of the present invention, when combining image data outputted from the radiation image detector that received radiation transmitted through the same subject each time the detector was shifted and changed in position along the predetermined shift axis, the image data representing the subject with respect to each position, if correction processing for eliminating an image distortion arising from the setting error is performed on at least a portion of the image data prior to combining the image data, while the correction processing is not performed if a situation arises in which the indication or the alarm needs to be provided, inappropriate correction processing due to increased setting error may be prevented.

In the mean time, the first time dependent degradation determination apparatus for a radiation image detector of the present invention includes a means for detecting a setting error of the imaging plane a plurality of times with the passage of time, a means for storing a plurality of setting errors detected, and a means for providing, when a fluctuation range of a plurality of setting errors stored exeeds a predetermined acceptable range, an indication or an alarm so indicating. Thus, the apparatus may implement the first time dependent degradation determination method for a radiation image detector of the present invention described above.

The second time dependent degradation determination apparatus for a radiation image detector of the present invention includes a means for detecting a setting error of the imaging plane a plurality of times with the passage of time, a means for storing a plurality of setting errors detected, and a means for providing, when a difference between a setting error detected first of a plurality of setting errors stored and at least one another setting error subsequently detected exceeds a predetermined acceptable difference, an indication or an alarm so indicating. Thus, the apparatus may implement the second time dependent degradation determination method for a radiation image detector of the present invention described above.

If the time dependent degradation determination apparatus for a radiation image detector of the present invention includes a radiation emission means for emitting radiation, through the common marker, to the radiation image detector, a shifting means for shifting the radiation image detector in the shift axis direction, a means for obtaining image data from the radiation image detector each time the shifting and radiation emission are performed, and a calculation means for calculating the inclination based on a positional relationship between each image of the marker represented by the image data obtained, the inclination may be detected accurately based on the marker images.

If the time dependent degradation determination apparatus for a radiation image detector of the present invention includes a radiation emission means for emitting radiation, through the common marker, to the radiation image detector, a shifting means for shifting the radiation image detector in the shift axis direction, a means for obtaining image data from the radiation image detector each time the shifting and radiation emission are performed, and a calculation means for calculating the displacement based on a positional relationship between each image of the marker represented by the image data obtained, the displacement may be detected accurately based on the marker images.

BRIEF DESCRIPTION OF THE DRAWINGS

FIG. 12 illustrates still another problem of conventional technology.

FIG. 13 illustrates a further problem of conventional technology.

FIG. 14 illustrates another problem of conventional technology.

FIG. 15 illustrates still another problem of conventional technology.

FIG. 16 illustrates a further problem of conventional technology.

DESCRIPTION OF THE PREFERRED EMBODIMENTS

Hereinafter, embodiments of the present invention will be described in detail with reference to the accompanying drawings.

Figure 1:
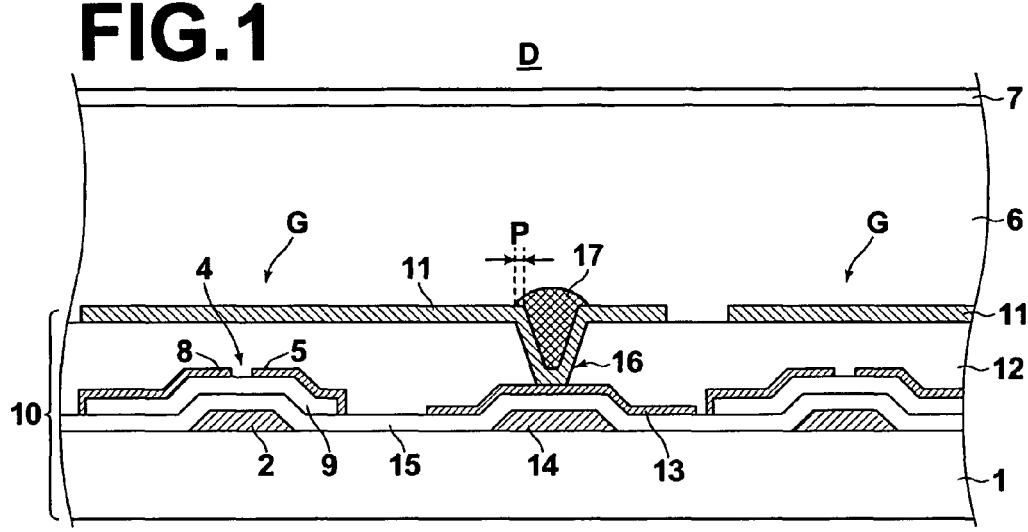
FIG. 1 is a partial side view of an example radiation image detector on which a time dependent degradation determination method is performed.

First, an example radiation image detector on which a time dependent degradation determination method according to the present invention is performed will be described. FIG. 1 is a partial cross-sectional view of such radiation image detector D, illustrating a portion around a pixel. As shown in FIG. 1, the radiation image detector D includes active matrix substrate 10 having multiple pixels G on which charge generation layer (photoelectric conversion layer) 6, having electromagnetic wave conductivity, and voltage application electrode (bias electrode, common electrode) 7, connected to a not shown high voltage power source, are formed on top of each other.

Each pixel G includes a switching element for reading out charges collected by a charge collection electrode, as described later. That is, one pixel G is formed for one switching element. The multiple pixels G are formed in a two-dimensional matrix, i.e., in the left/right direction and a direction perpendicular to the plane of FIG. 1. Charge generation layer 6 generates therein a charge (electron-hole) by receiving an electromagnetic wave, such as an X-ray. That is, charge generation layer 6 has electromagnetic wave conductivity and converts image information represented by radiation to charge information. Charge generation layer 6 is formed, for example, of selenium based a-Se.

Active matrix substrate 10 includes glass substrate 1, gate electrode 2, gate insulating film 15, upper storage capacitor electrode 13, semiconductor layer 9, source electrode 8, drain electrode 5, interlayer insulating film 12, and charge collection electrode 11. Thin film transistor 4 as a switching element (TFT switch) is formed of gate electrode 2, gate insulating film 15, source electrode 8, drain electrode 5, semiconductor layer 9, and the like. In TFT switch 4, source electrode 8 and drain electrode 5 are connected to a data wire (not shown) which is one of electrode wires disposed in a grid pattern and upper storage capacitor electrode 13. Semiconductor layer 9 makes contact between source electrode 8, drain electrode 5, and gate electrode 2.

Glass substrate 1 is a support substrate formed, for example, of alkali free glass. Gate insulating film 15 is formed of $SiN_x$, $SiO_x$, or the like. Gate insulating film 15 is provided so as to cover gate electrode 2 and lower storage capacitor electrode 14, in which the portion over gate electrode 2 acts as a gate insulating film of TFT switch 4 and the portion over lower storage capacitor electrode 14 acts as a dielectric layer of a charge storage capacitor. That is, the charge storage capacitor is constituted by a stacked area of lower storage capacitor electrode 14, formed in the same layer as gate electrode 2, and upper storage capacitor electrode 13.

Gate electrode 2 and lower storage capacitor electrode 14 are provided on glass substrate 1. Semiconductor layer 9 is formed above gate electrode 2 via gate insulating film 15, and source electrode 8 and drain electrode 5 are formed above semiconductor layer 9. Gate insulating film 15 is disposed above lower storage capacitor electrode 14 and upper storage capacitor electrode 13 is provided above gate insulating film 15.

Interlayer insulating film 12 is formed, for example, of an acrylic resin having photosensitivity or the like, and electrically insulates and isolates each TFT switch 4. Contact hole 16 is formed through interlayer insulating film 12. Charge collection electrode 11 is connected to upper storage capacitor electrode 13, which is a signal extraction electrode, through contact hole 16.

Charge collection electrode 11 is formed, for example, of an amorphous transparent conductive oxide film, and stacked over source electrode 8, drain electrode 5, and upper storage capacitor electrode 13. Charge collection electrode 11 and charge generation layer 6 are in electrical communication with each other, allowing charges generated in charge generation layer 6 to be collected by charge collection layer 11. In order to collect charges generated in charge generation layer 6 and to output to the outside via TFT 4 and a not shown data wire, charge collection layer 11 is electrically connected to drain electrode 5 of TFT switch 4 and a charge storage capacitor. Charge generation layer 6 is formed directly above charge collection layer 11 in order to pass charges to charge collection layer 11.

Potential grading member 17 is disposed in contact hole 16 and an area around contact hole 16 such that the potential grading member 17 fills up contact hole 16. The area around contact hole 16 (the area denoted by "P" in FIG. 1) refers to an area within about 5 μm from the edge of the contact hole. Preferably, potential grading member 17 is provided with a curvature that eases the edge of contact hole 16.

Potential grading member 17 may be formed of an organic resin having a low dielectric constant and a coefficient of thermal expansion which is approximately the same as that of the material forming the charge generation layer 6, and specific examples include photosensitive resins, such as novolac resin, epoxy resin, acrylic resin, urethane resin, polyester resin, polyimide resin, and polyolefin resin.

A not shown high voltage power source is connected between bias electrode 7 and lower storage capacitor electrode 14. The high voltage power source applies a voltage between bias electrode 7 and lower storage capacitor electrode 14, thereby generating an electric field between the bias electrode 7 and the charge collection electrode 11 via the charge storage capacitor. Charge generation layer 6 and the charge storage capacitor are electrically connected in series. Thus, while a bias voltage is applied to bias electrode 7, charge generation layer 6 exposed to radiation, such as X-ray, generates charges (electron-hole pairs) therein. The electrons generated in charge generation layer 6 move toward the positive electrode and the holes generated in charge generation layer 6 move toward the negative electrode. As a result, electric charges are stored in the charge storage capacitor.

A radiation image detector D as a whole includes two-dimensionally arranged charge collection electrodes 11, the charge storage capacitors individually connected to charge collection electrodes 11, and TFT switches 4 individually connected to the charge storage capacitors. This allows two-dimensional electromagnetic wave information to be temporarily stored in the charge storage capacitors and TFT switches 4 to be sequentially scanned, whereby two-dimensional charge information can be readout as elecrical image data (image signal).

As described above, in the radiation image detector D, charges are stored with respect to each pixel G. A plane parallel to the plane on which pixels G are arranged, i.e., charge generation layer 6 is, herein, referred to as the imaging plane.

Next, processing for detecting setting errors of an imaging plane of a radiation image detector related to the present invention, in particular, inclination of the two-dimensional pixel matrix of the imaging plane relative to the shift axis of the radiation image detector and, based on the detected inclination, eliminating misalignment due to the inclination at a joint of a combined image will be described.

Figure 2:
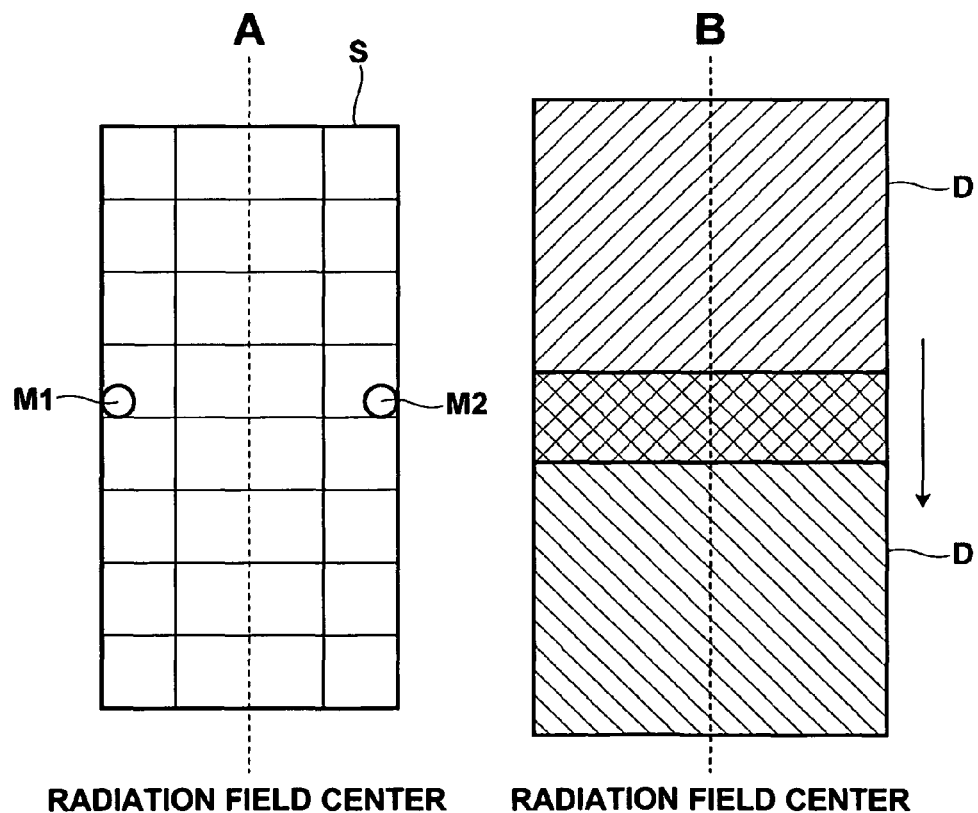
FIG. 2 schematically illustrates radiation image taking for detecting an inclination of an imaging plane.
Figure 10:
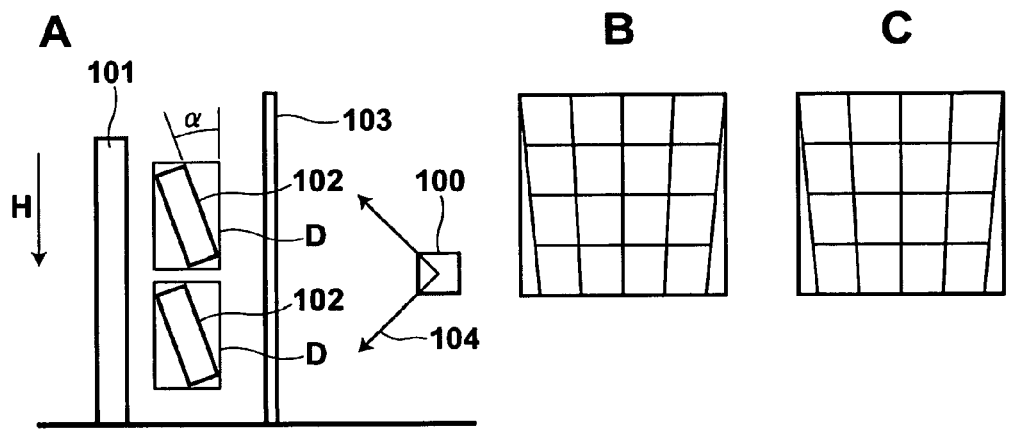
FIG. 10 illustrates a problem of conventional technology.
Figure 11:
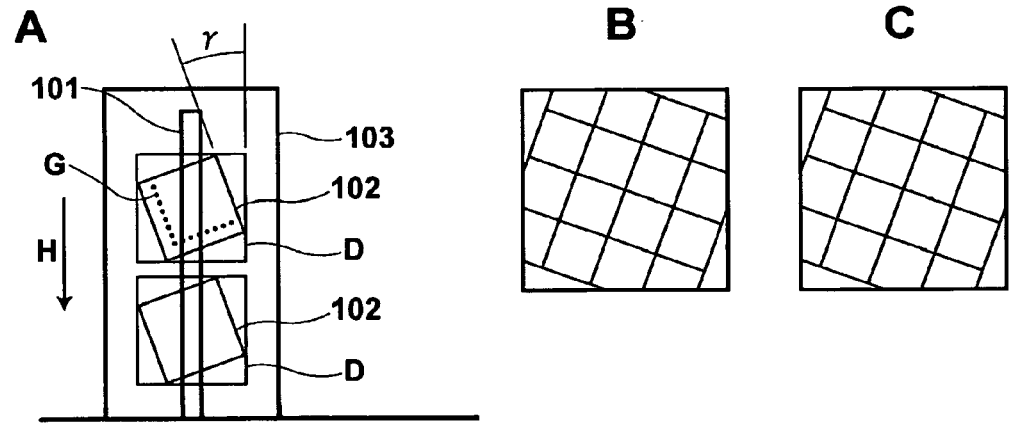
FIG. 11 illustrates another problem of conventional technology.

First, a marker is imaged by an imaging system having the basic structure as shown in A of FIG. 10 and A of FIG. 11. At this time, in place of grid 103 shown in A of FIG. 10, a subject plane S like that shown in A of FIG. 2 is placed, and two markers M1 and M2, which are spaced from each other by a predetermined distance in the horizontal direction, are held on the subject plane S. The radiation image detector D held by stand 101 is placed behind the subject plane S, i.e., on the side opposite to radiation source 100.

Then, as shown in B of FIG. 2, the panel type quadrangular (rectangular or square) radiation image detector D is shifted downward. The radiation image detector D, standing still before and after the shifting, is exposed by radiation transmitted through markers M1 and M2, whereby a radiation image of markers M1 and M2 is taken two times. Here, the imaging may be achieved, for example, by swiveling the radiation source or expanding the radiation emission field to cover an area corresponding to two panels.

In the two imaging operations, the radiation image detector D is positioned at the place indicated by the diagonally right up hatching shown in B of FIG. 2 for the first imaging operation, and at the place indicated by the diagonally left up hatching shown in B of FIG. 2 for the second imaging operation, so that markers M1 and M2 are imaged in each of the two imaging operations in a duplicated manner. Further, in each of the imaging operations, the radiation image detector D and the subject plane S are set such that the center positions of the radiation image detector D and the subject plane S in the width direction are aligned with the center of the exposure field of the radiation (center in the transverse direction). The two markers M1 and M2 are disposed at positions opposite to and equal, in distance, from the center of the exposure field.

After the first imaging operation, the reading operation described above is performed prior to the second imaging operation and image data representing a radiation image of markers M1 and M2 are acquired. Another reading operation is also performed after the second imaging operation and similar image data are obtained.

Next, a method of obtaining the inclination angle α shown in A of FIG. 10 will be described. Radiation images represented by image data obtained by the two reading operations are like those shown in A of FIG. 3. In the drawing, the upper radiation image is an image obtained by the first imaging/reading operation and the lower radiation image is an image obtained by the second imaging/reading operation. Markers M1 and M2 are recorded in each radiation image, but if imaging plane 102 is inclined by the angle α with respect to the panel surface as shown in A of FIG. 10, images of markers M1 and M2 are misaligned between the two radiation images. The inclination of the imaging plane 102 occurs due to an assembly error or the like, when the structure like that shown in FIG. 1 is assembled and fixed in a quadrangular panel housing (the same applies to angle γ to be described later). On the other hand, if the inclination of the angle α is not present in the imaging plane, the two radiation images are like those shown in B of FIG. 3. Therefor, from the relationship between A and B of FIG. 3, the angle α can be obtained.

Figure 3:
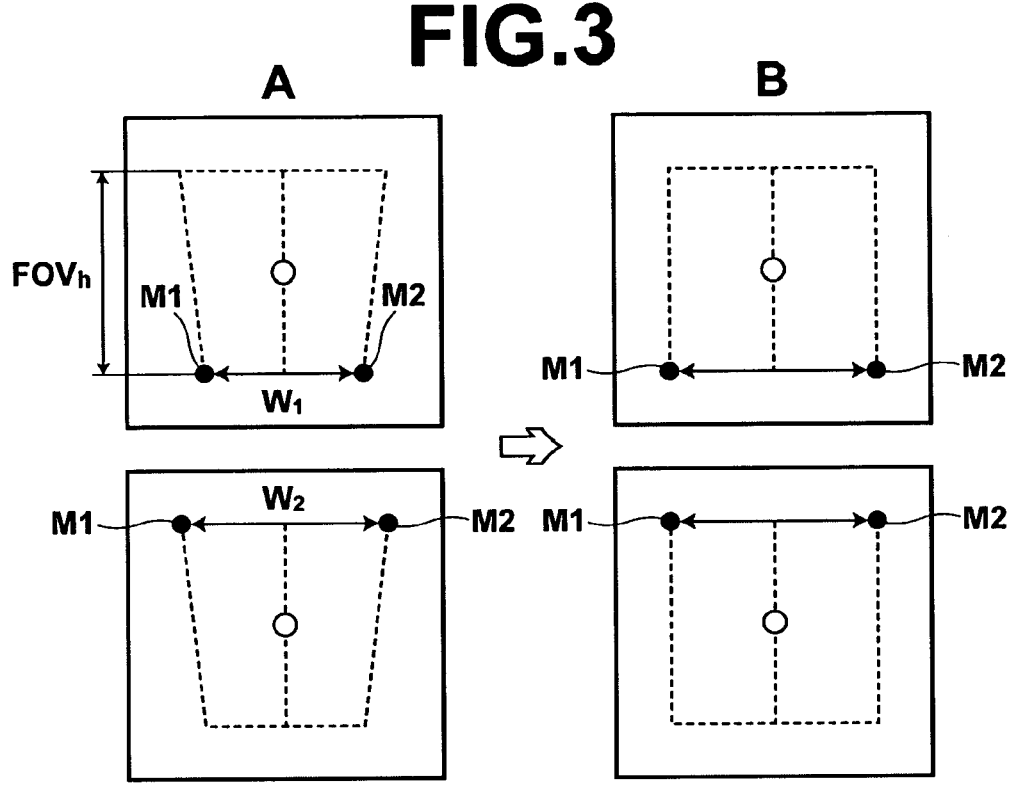
FIG. 3 is a schematic view illustrating recorded aspects of radiation images when the imaging plane of a radiation image detector is inclined and when the detector is not inclined.
Figure 4:
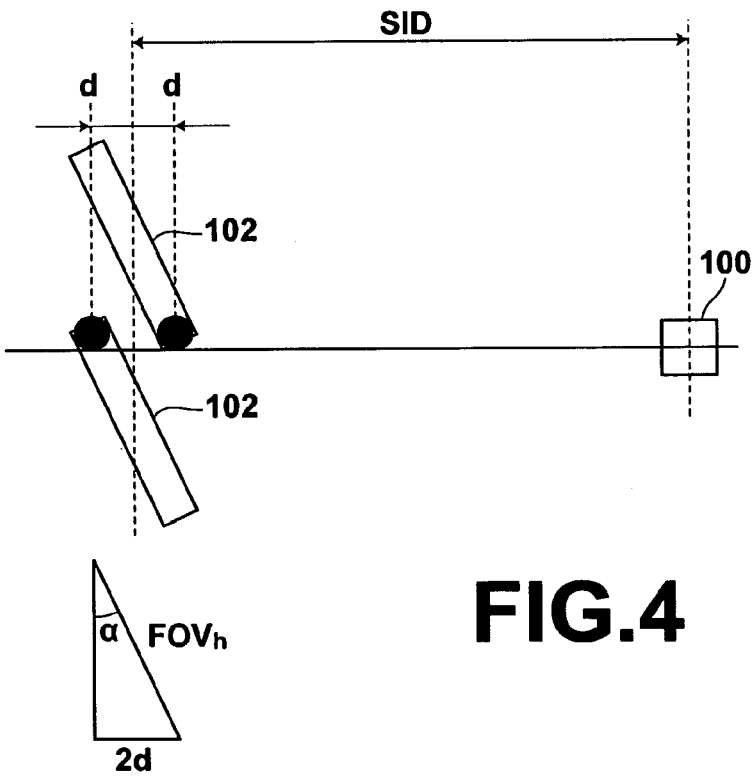
FIG. 4 is a schematic side view illustrating recording (imaging) of a radiation image.

Here, it is assumed that the distances between markers M1 and M2 in the image obtained by the first imaging and in the image obtained by the second imaging are $w_1$ and $w_2$ respectively. Further, as shown in FIG. 4, the distance from the center of the imaging plane to markers M1 and M2 in the direction in which the radiation is emitted is assumed to be d, and the distance from the radiation source 100 to the center of the imaging plane is assumed to be SID. Furthermore, as shown in FIGS. 3 and 4, twice the distance from the center of the imaging plane to a midpoint between the markers M1 and M2 on the imaging plane 102 is assumed to be $FOV_h$. The relationship among the distances described above is represented by Formula 1 below, and Formula 2 can be derived therefrom.

$$\begin{cases} w_1 \times \dfrac{SID+d}{SID} = w_2 \times \dfrac{SID-d}{SID} \\ \sin\alpha = \dfrac{2d}{FOV_h} \end{cases} \quad \text{[Formula 1]}$$

$$\sin\alpha = \dfrac{2(w_2 - w_1) \cdot SID}{FOV_h \cdot (w_1 + w_2)} \quad \text{[Formula 2]}$$

From each of the distances described above, the inclination angle of imaging plane 102 can be obtained based on Formula 2. To be more exact, the difference between $w_1$ and $w_2$ varies with the positional relationship in height between the radiation image detector D and the radiation source 100, and hence the derived angle $\alpha$ also varies. However, the value of d is normally sufficiently small relative to SID, and the variation may be ignored to obtain the angle through approximation by Formula 2.

Next, a method of obtaining the inclination angle γ shown in A of FIG. 11 will be described. Radiation images represented by image data obtained by the two reading operations are like those shown in A of FIG. 5. In the drawing, the upper radiation image is an image obtained by the first imaging/reading operation and the lower radiation image is an image obtained by the second imaging/reading operation. Markers M1 and M2 are recorded in each radiation image, but if two-dimensional matrix of pixels G is inclined by the angle γ with respect to one side of the panel as shown in A of FIG. 11, images of markers M1 and M2 are misaligned between the two radiation images. On the other hand, if the inclination of the angle γ is not present in the imaging plane, the two radiation images are like those shown in B of FIG. 5. Therefor, from the relationship between A and B of FIG. 5, the angle γ can be obtained.

Figure 5:
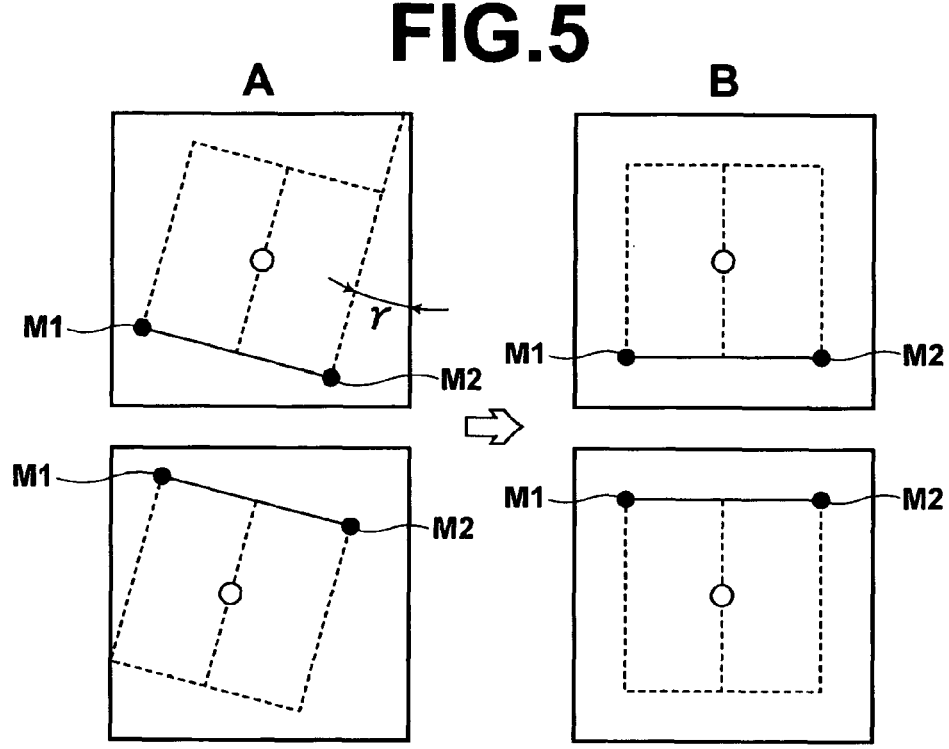
FIG. 5 is a schematic view illustrating recorded aspects of radiation images when the imaging plane of a radiation image detector is inclined and when the detector is not inclined.

That is, when a square grid with one side corresponding to the line segment connecting the centers of images of marker M1 and M2 is assumed, as shown by dashed lines in FIG. 5, shifting one of the radiation images in the longitudinal and transverse directions relative to the other radiation image such that the center positions of the grid in the images are aligned to each other, the angle γ can be obtained from the amounts of shift in the two directions.

Figure 6:
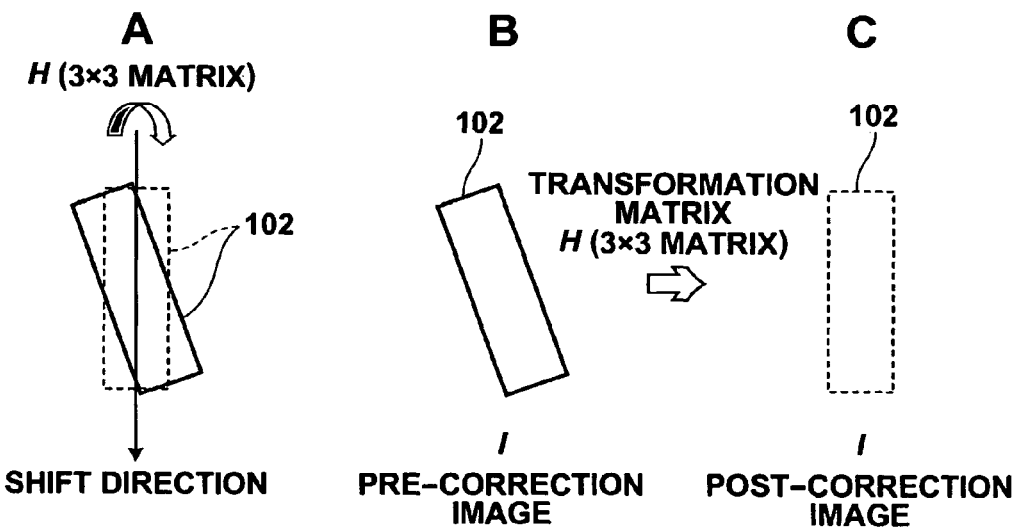
FIG. 6 is a schematic view illustrating an example image correction method.

Next, processing for correcting distortion of radiation images arising from the inclinations based on the angles $\alpha$ and γ obtained in the manner as described above will be described. As an example case, it is assumed that the imaging plane 102 is inclined in the direction of the angle $\alpha$, as illustrated by the solid line in A of FIG. 6, and a subject is imaged by the first and second imaging operations under the state shown in B of FIG. 6. In this case, if the radiation images of the subject record and read out from the imaging plane 102 can be corrected like radiation images taken under the state shown in C of FIG. 6, the distortion of the images due to the inclination by the angle $\alpha$ can be eliminated, whereby combining of the two images does not cause misalignment at the joint. It should be noted that, in this example, the images are also corrected to eliminate the distortion of the images due to the inclination in the direction of angle γ of imaging plane 102.

Here, it is a prerequisite condition that the shifting of the radiation image detector D has repeatablility, and the radiation image detector D is shifted during the imaging of a subject in the same manner as that when the angles $\alpha$ and γ are obtained.

Next, a method of obtaining parameters used in the correction will be described. Here, a method of obtaining a transformation matrix from the obtained angles $\alpha$ and γ will be described. More specifically, a method in which four or more of representative points are set and a transformation matrix is obtained based on the correspondence between the representative points before and after the transformation will be described. First, in order to correct the image distortion due to the inclination of the imaging plane in the direction of the angle $\alpha$, it is only necessary to obtain parameters for correcting four representative points shown by black circles in A of FIG. 7 (which are assumed, here, to form a square in a correctly recorded state) to the four representative points shown in B of FIG. 7. The lengths of the deformed lower and upper sides of the uncorrected square are assumed to be $w_1$ and $w_2$ espectively, and the lengths of the lower and upper sides of the corrected square are assumed to be $w_1'$ and $w_2'$ respectively. Then, the relationships expressed by Formulae 3 and 4 below are established. The variables other than $w_1$, $w_2$, $w_1'$ and $w_2'$ are the same as those described above.

$$W_1' = W_1 \times \dfrac{SID+d}{SID} \quad \text{[Formula 3]}$$

$$\sin\alpha = \dfrac{2d}{FOV_h}$$

$$W_2' = W_2 \times \dfrac{SID-d}{SID} \quad \text{[Formula 4]}$$

$$\sin\alpha = \dfrac{2d}{FOV_h}$$

The relationships of Formulae 5 and 6 below are derived from Formulae 3 and 4 respectively.

$$W_1' = W_1 \times \left(1 + \dfrac{FOV_h \cdot \sin\alpha}{2SID}\right) \quad \text{[Formula 5]}$$

$$W_2' = W_2 \times \left(1 - \dfrac{FOV_h \cdot \sin\alpha}{2SID}\right) \quad \text{[Formula 6]}$$

Figure 7:
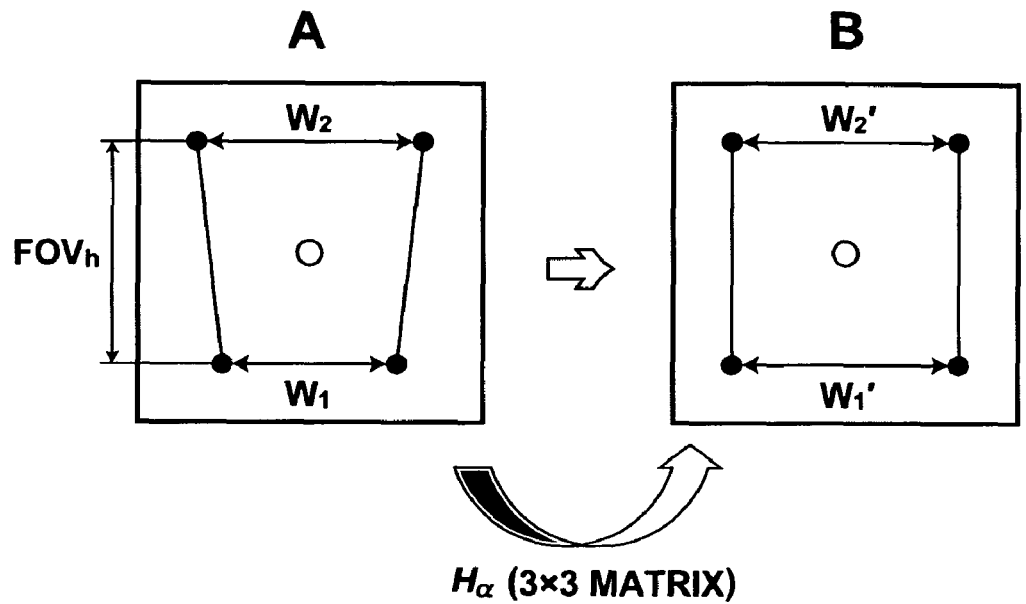
FIG. 7 is a schematic view illustrating another example image correction method.

Then, the value in the parenthesis in the right side of each of Formulae 5 and 6 is calculated based on the obtained angle $\alpha$ and known values of SID and $FOV_h$, and the calculated values are used as the parameters for transforming $w_1$ into $w_1'$ and $w_2$ into $w_2'$ respectively. Using these parameters, a (3×3) matrix $$H_\alpha \quad \text{[Formula 7]}$$

for transforming image data representing a two-dimensional radiation image based on the relationship between A and B of FIG. 7 is obtained.

Figure 8:
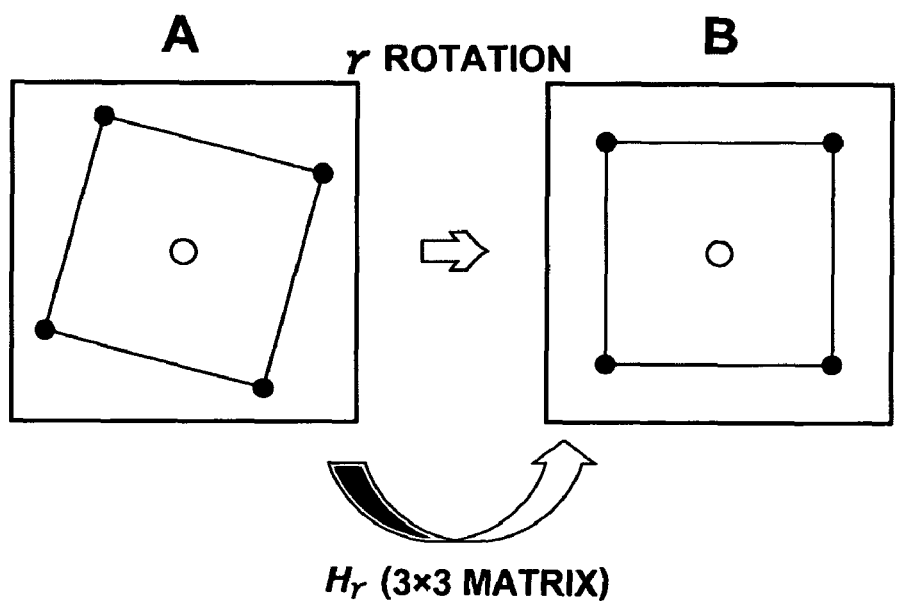
FIG. 8 is a schematic view illustrating still another example image correction method.

Further, A and B of FIG. 8 show a relationship between radiation images before and after rotated by the angle γ described above. In this case, a (3×3) matrix $$H_\gamma \quad \text{[Formula 8]}$$

for transforming image data representing a two-dimensional radiation image based on the rotational relationship between A and B of FIG. 8 is obtained. The matrix for transforming an image according to a rotational relationship can be obtained by any known methods.

Since the inclinations of imaging plane 102 in the two directions of angles $\alpha$ and γ are summing of linear phenomena, the two types of inclinations can be combined by multiplication of the matrixes as shown by Formula 9 below.

$$H = H_\alpha H_\gamma \text{ or } H = H_\gamma H_\alpha \quad \text{[Formula 9]}$$

Then, when image data representing a radiation image of a subject obtained by the first imaging/reading operation are transformed using the post multiplication matrix in Formula 9

$$H \qquad \text{[Formula 10]}$$

as the transformation matrix, the transformed image data are free from distortions arising from inclinations of imaging plane 102 in the directions of the angles α and γ. The same result may be obtained when image data representing a radiation image of the subject obtained by the second imaging/reading operation is transformed. Consequently, if two images are combined after being subjected to the transformation, misalignment at the joint of a combined long length radiation image may be prevented.

Figure 9:
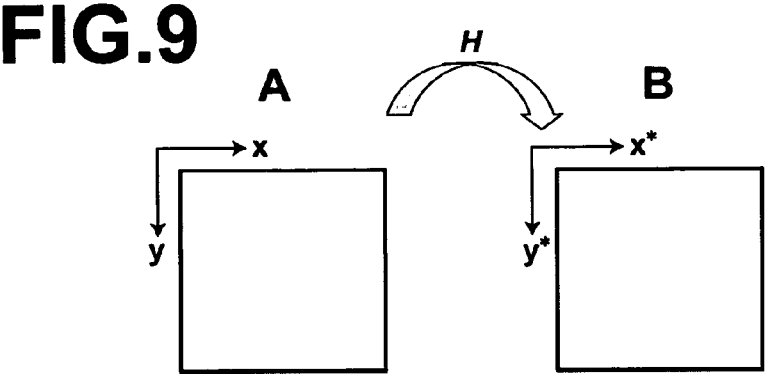
FIG. 9 illustrates image coordinate systems before and after image correction.

As a specific example of image transformation processing using the aforementioned transformation matrix, a two-dimensional projective transformation will be described. As shown in A and B of FIG. 9, coordinate systems before and after the two-dimensional projective transformation using the transformation matrix $$H \qquad \text{[Formula 11]}$$

are assumed to be an xy coordinate system and an x*y* coordinate system respectively. Generally, the two-dimensional projective transformation may be expressed, in a homogeneous coordinate system, by Formula 12 below.

$$(x \quad y \quad 1) \begin{pmatrix} a & b & p \\ c & d & q \\ t_x & t_y & s \end{pmatrix} = (X^* \quad Y^* \quad w^*) \qquad \text{[Formula 12]}$$

where $X^* = w^* x^*$, $Y^* = w^* y^*$ $$H = \begin{pmatrix} a & b & p \\ c & d & q \\ t_x & t_y & s \end{pmatrix}$$

It should be noted that the homogeneous coordinate system handles a n-dimensional problem as a (n+1)-dimensional problem to simplify and generalize the calculation. The transformation matrix H has nine components, however, has eight degrees of freedom. The transformation matrix $$H \qquad \text{[Formula 13]}$$

can therefore be found when correspondence of at least four points are obtained (that is, two formulae with respect to the xy coordinates are obtained for correspondence of each point).

After the transformation matrix $$H \qquad \text{[Formula 14]}$$

is obtained, then with the original data being assumed to be $$I \qquad \text{[Formula 15]}$$

and corrected image data being assumed to be $$I' \qquad \text{[Formula 16]}$$

corrected image data may be obtained as follows.

$$I' = HI \qquad \text{[Formula 17]}$$

In the example described above, the image data are corrected based on the obtained inclination angles α and γ of imaging plane 102 to eliminate the image distortion due to the inclinations, but such correction may not be carried out and the position of imaging plane 102 may be corrected manually to eliminate the obtained inclination angles α and γ of imaging plane 102. Further, the position of the imaging plane 102 may be corrected automatically based on the inclination angles α and γ with an imaging plane position correction means incorporated in the radiation image detector D.

As for markers usable in the invention, the aforementioned grid is also applicable, other than the markers M1 and M2 representing two points described above.

Next, processing for correcting image distortions arising from the aforementioned inclination angles α and γ and the displacements Δy and Δx shown respectively in FIGS. 15 and 16 will be described. For the purpose of clarity and convenience of explanation, one of the inclination angles α will be referred to as the "pitching inclination angle" and the radiation image detector D will be sometines referred to simply as a "panel" in the following description. The image correction method described herein by way of an example is a method that, when a position in an image obtained with a panel inclined and/or displaced is expressed in an an x-y coordinate system and a position in a final corrected image is expressed in an x"-y" coordinate system, determines the position (x", y") in the x"-y" coordinate system for image data at a position (x,y) in the x-y coordinate system.

Figure 17:
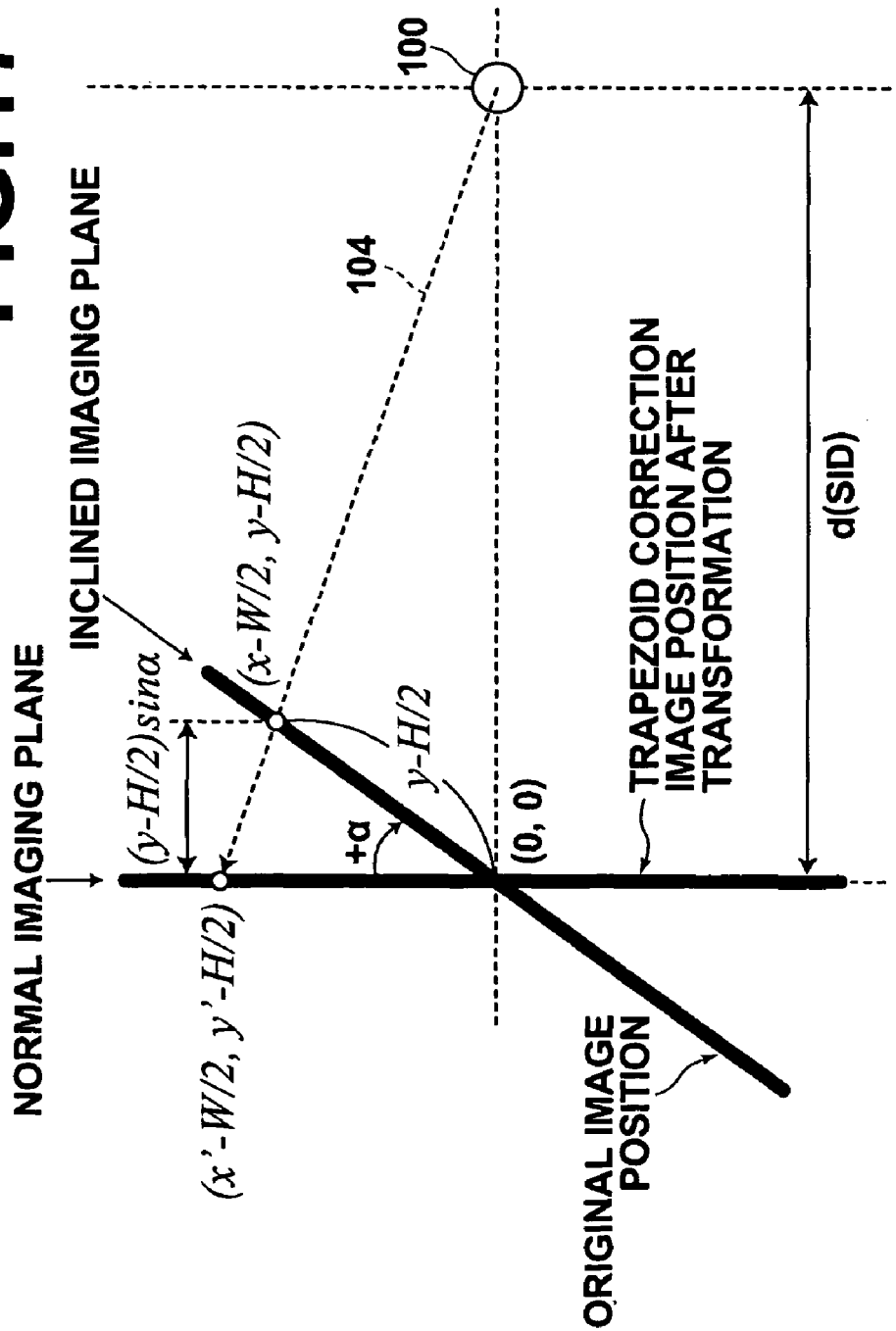
FIG. 17 is a schematic view illustrating an example image correction method.

First, a method of correcting a obtained image deformed in a trapezoidal shape as illustrated in FIG. 10 since the panel is inclined by a pitching inclination angle α, as illustrated in FIG. 17, will be described. Hereinafter, this correction is referred to as "trapezoid correction". In this example, it is assumed that the imaging plane is not inclined relatively to the panel, and the pitching inclination angle α of the panel directly corresponds to the inclination angle α of the imaging plane, i.e., two-dimensional pixel matrix. In FIG. 17, the term "normal imaging plane" refers to an imaging plane without pitching inclination angle α. The trapezoid correction is a correction that, when a position on the normal imaging plane is expressed in an x'-y' coordinate system, determines the position (x',y') in the x'-y' coordinate system for image data at a position (x,y) in the x-y coordinate system.

where:
α is the pitching inclination angle (−90°<α<+90°);
x,y are coordinates on the inclined panel (actual image data);
x',y' are coordinates in an image after being subjected to the trapezoid correction and straigtened up;
d is the SID (source image distance);
W is the image width; and
H is the image height.

From FIG. 17, an enlargement/reduction factor of the image in the x-direction due to the presence of the pitching inclination angle α is as follows.

$$d:d-y \sin \alpha = x':x \qquad \text{[Formula 18]}$$

Moving the origin of the coordinate system from a position on the inclined imaging plane, which a normal line crossing through the center of the radiation source 100 hits, to a position on the normal imaging plane, which a normal line crossing through the center of the radiation source 100 hits, i.e., the point (0,0) shown in FIG. 17, the following may be derived from Formula 18 above.

$$d:d-(y-H/2)\sin \alpha = x'-W/2:x-W/2 \qquad \text{[Formula 19]}$$

Therefore, the relationship between the position (x,y) and the position (x',y') is as follows.

$$x' = \frac{d}{d-(y-H/2)\sin\alpha}(x-W/2)+W/2 \qquad \text{[Formula 20]}$$

$$y' = y$$

To be more precise, the image may also be enlarged or reduced in the y-direction; however, it is assumed here that the enlargement or reduction of the image in the y-direction is sufficiently small and can be approximated as y'=y.

Next, correction of image distortions arising from the inclination angle γ shown in FIGS. 11 and 13, and the displacements Δy and Δx shown respectively in FIGS. 15 and 16 will be discussed. In this example, the displacements Δy and Δx are expressed as Δx=$t_x$ and Δy=$t_y$. The conditions here are as follows:

(x,y) are coordinates on original image;
(x',y') are coordinates on the image after trapezoid correction;
(x",y") are coordinates on the final corrected image;
$t_x$ is the amount of translation in the x direction;
$t_y$ is the amount of translation in the y direction; and
γ is the rotational angle in the xy plane.

The relationship between the position (x,y) before the trapezoid correction and the position (x',y') after the trapezoid correction is as expressed by Formula 20 above. When a position in a final corrected image is expressed in x"-y" coordinate system described above, the relationship between the position (x",y") in the coordinate system and the position (x',y') after the trapezoid correction is as follows.

$$\begin{pmatrix} x'' \\ y'' \\ 1 \end{pmatrix} = \begin{pmatrix} 1 & 0 & t_x \\ 0 & 1 & t_y \\ 0 & 0 & 1 \end{pmatrix} \begin{pmatrix} \cos\gamma & \sin\gamma & 0 \\ -\sin\gamma & \cos\gamma & 0 \\ 0 & 0 & 1 \end{pmatrix} \begin{pmatrix} x' \\ y' \\ 1 \end{pmatrix}$$ [Formula 21]

As described above, performance of the two transformation operations represented by Formulae 20 and 21 may transform the image data at the position (x,y) into the image data at the position (x",y"). Consequently, if a correction is performed in which original image data of the position (x,y) obtained by performing reading operation on the radiation image detector D with respect to each radiation emission are transformed into image data of the position (x",y") through the aforementioned two transformation operations, a misalignment, when a long length image is formed by combining the corrected image data, at the joint may be prevented.

Figure 18:
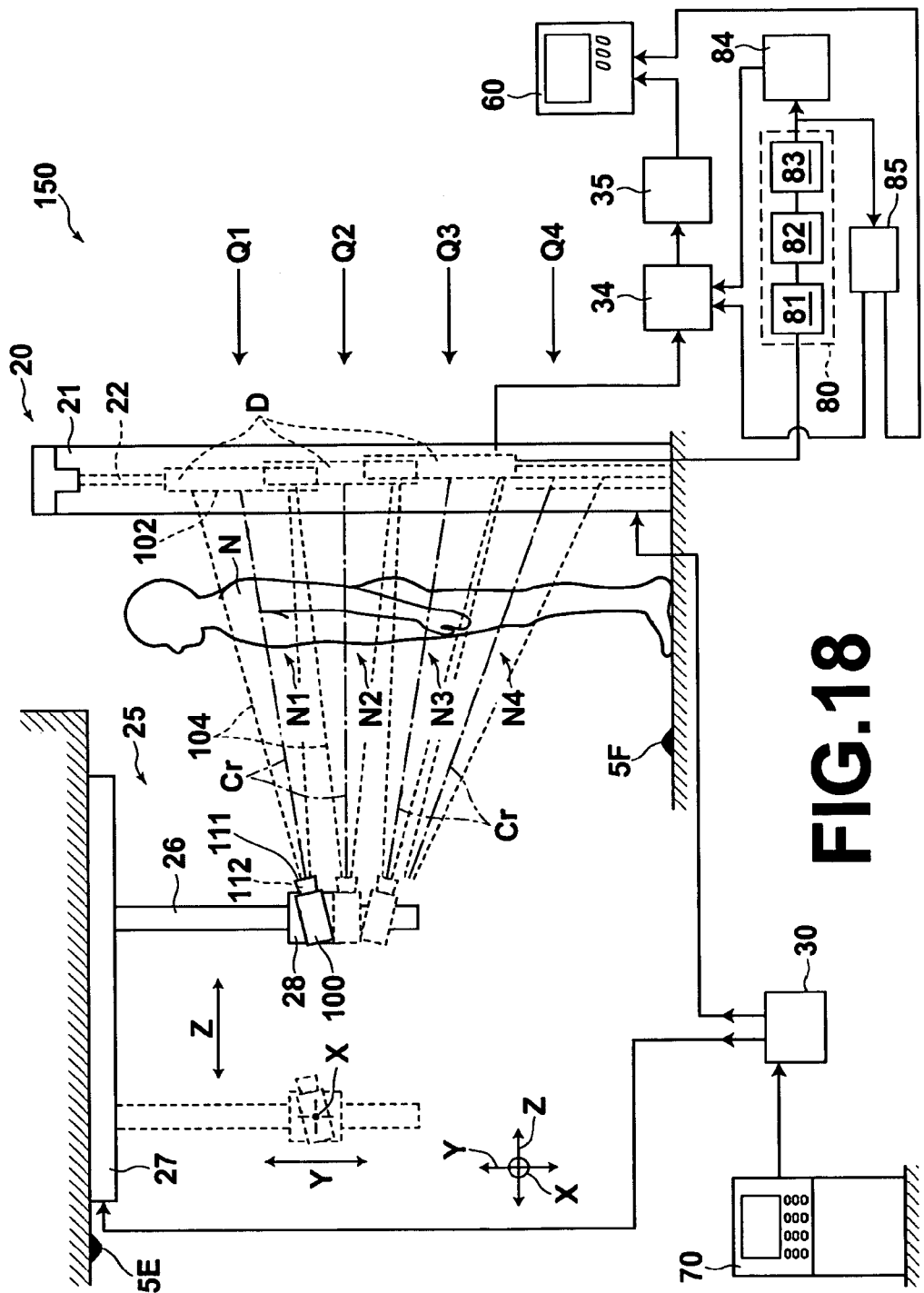
FIG. 18 is a schematic configuration diagram of a time dependent degradation determination apparatus for a radiation image detector according to an embodiment of the present invention.

An apparatus for implementing the image plane setting error detection method and the image correction method described above will now be described. FIG. 18 is a schematic configuration diagram of a radiation image taking apparatus 150 which includes a time dependent degradation determination apparatus for a radiation image detector according to an embodiment of the invention, as well as an imaging plane setting error detection apparatus and an image correction apparatus. Radiation image taking apparatus 150 is adapted to sequentially image a plurality of adjacent areas N1, N2, - - - of a subject N using one radiation source 100 and one radiation image detector D and to obtain a long length radiation image representing a large part of the subject N by combining a plurality of images so obtained.

More specifically, radiation image taking apparatus 150 includes radiation source 100 that emits radiation 104 from emission window 111 toward an exposure range defined by collimator 112, the radiation image detector D having imaging plane (radiation detection surface) 102 that receives and detects radiation 104 transmitted through the subject N, detector shifting unit 20 that shifts the radiation image detector D along the subject N, and radiation source positioning unit 25 that places radiation source 100 such that emission window 111 is disposed at a desired position with a desired orientation. In FIG. 18, the emission center axis of each exposure range of radiation 104 defined by collimator 112 is denoted by "Cr".

The radiation image detector D has a basic structure like that described above with reference to FIG. 1. The radiation image detector D detects radiation 104 transmitted through the subject N and converts the radiation to an electrical signal to output image data representing a radiation image of the subject N.

The detector shifting unit 20 includes two supporting columns 21 standing in a vertical direction (arrow Y directions in the drawing) from a floor surface 5F and holds the radiation image detector D therebetween, and a shift mechanism 22 that shifts the radiation image detector D in the vertical direction, i.e., in a long lenth direction. As for shift mechanism 22, a mechanism that supports the radiation image detector D by a known linear slide mechanism or the like, and shifts the radiation image detector D using a drive source, such as a motor or the like, may be employed.

When imaging is performed for obtaining radiation images to be combined, the subject N is disposed along the shifting direction of the radiation image detector D. That is, the imaging is performed with the subject N standing on the floor surface.

Radiation source positioning unit 25 is a unit that holds and moves the radiation source 100 so as to face imaging plane 102 of the radiation image detector D, i.e., substantially in the arrow Z directions in the drawing with the subject N being placed therebetween. The radiation source positioning unit 25 includes a supporting column 26 extending in the vertical direction from ceiling 5E, a ceiling base 27 for moving supporting column 26 along the ceiling 5E in the arrow Z directions in the drawing, and rotating base 22 that engages with supporting column 26, is movable in the arrow Y directions in the drawing, and rotatable about an axis which is perpendicular to the plane of the drawing. The radiation source 100 is mounted on rotating base 28. In this way, radiation source 100 is movable in the vertical directions (the arrow Y directions in the drawing) and in the left/right directions (in the arrow Z directions in the drawing), and is rotatable about an axis passing through the substantial center of radiation source 100 and parallel to the X-axis in the drawing. Radiation source positioning unit 25 may be formed using a known linear slide mechanism, a rotary mechanism, and a drive source, such as a motor.

Radiation image taking apparatus 150 further includes a long length imaging control unit 30 that controls the operation of detector shifting unit 20 and the radiation source positioning unit 25. The long length imaging control unit 30 controls the operation of the detector shifting unit 20 such that the radiation image detector D is sequentially shifted along the direction in which the subject N extends to positions Q1, Q2, - - - for taking radiation images. At the same time, the long length imaging control unit 30 controls the operation of radiation source positioning unit 25 to position the radiation source 100 such that the direction of radiation 104 emitted from the radiation source 100 is oriented toward imaging plane 102 of the radiation image detector D when the radiation image detector D is positioned at each of the positions described above. As the radiation source 100 is driven under this state, adjacent areas N1, N2, - - - of the subject N are sequentially imaged and image data representing each of a plurality of image portions representing the entirety of the subject N are obtained for each imaging operation.

Radiation image taking apparatus 150 further includes image combining unit 35 that combines the image data obtained in each imaging to provide a long length radiation image representing the entirety of the subject N. The long length radiation image obtained in the manner as described above is displayed on an image display unit 60 that includes, for example, a CRT display or the like.

The overall operation of radiation image taking apparatus 150 is controlled through console 70. Therefore, information of the subject N, imaging conditions for obtaining a long length radiation image, and the like are inputted to console 70, and the information of these data are inputted to the long length imaging control unit 30, an imaging adjustment unit (not shown) for setting the radiation emission range defined by collimator 112, and the like. The imaging adjustment unit adjusts the position of radiation source 100, condition of collimator 112, position of the radiation image detector D, and the like at each imaging operation such that radiation images of a predetermined size, to be combined, are obtained through, for example, four imaging operations. Then, imaging operations for taking four radiation images are performed in response to an instruction from console 70.

The size of the four radiation images obtained through the four imaging operations may be determined by defining the radiation emission range through collimator 112, as described above, or by adjusting the length and width of each image portion by cutting out a portion of each radiation image obtained through each imaging operation.

Next, processing for detecting a setting error of the imaging plane of the radiation image detector D performed in the apparatus will be described. First, a description will be made of a case in which the processing is performed by automatic setting error detection device 80. The automatic setting error detection device 80 includes a calibration image input unit 81 that obtains image data from the radiation image detector D, a marker detection unit 82 that receives output of the calibration image input unit 81, and setting error detection unit 83 that receives output of marker detection unit 82. Output of setting error detection unit 83 is inputted to parameter calculation unit 84.

When detecting a setting error of the imaging plane, imaging operations and reading operations for reading radiation images taken through the imaging operations for detecting a setting error are performed separately from a usual imaging operation of a subject through, for example, an imaging menu inputted from console 70. A series of operations from that described above and that for obtaining a correction parameter is herein referred to as "calibration", and radiation images obtained by the calibration are referred to as "calibration images". During the calibration, the radiation image detector D is sequentially shifted to the positions Q1, Q2, - - - and the radiation image detector D standing still at each position is exposed to radiation 104 transmitted through markers, such as markers M1 and M2 described above.

At this time, imaging is performed such that the image of the markers M1 and M2 is commonly captured within the overlapping area of the radiation image detector D when it is positioned at each of two adjacent positions Q1 and Q2. The same applies to other two adjacent positions Q2 and Q3, and Q3 and Q4. Here, the markers may be arranged at an appropriate interval in the vertical direction such that the image of the common markers is captured within any overlapping area on the radiation image detector D positioned at each of the two positions, or the positions Q1, Q2, - - - may be defined precisely in advance and the markers may be placed in overlapping positions corresponding to each of the positions Q1, Q2, - - - , whereby the imaging may be performed in the manner as described above.

Preferably, when an instruction to take calibration images is issued via the imaging menu, the imaging range of each radiation image, including the markers, width of each overlapping area, and framing of each image are automatically set to predetermined values. Further, an arrangement may be adopted in which the markers described above are provided on a screen, and when the screen is set in a predetermined receptacle for taking calibration images, a screen detection signal is generated and the signal serves as a trigger for displaying various menus, for example, on a display of console 70 for taking the calibration images.

At the time of taking the calibration images, when imaging operations are performed by placing the radiation image detector D at each of the positions Q1, Q2, - - - , a reading operation is performed on the radiation image detector D with respect to each imaging operation, and image data representing the calibration image with the markers is outputted from the radiation image detector D. Calibration image input unit 81 of automatic setting error detection device 80 receives the image data and sends the data to the marker detection unit 82. The marker detection unit 82 detects the positions of the markers based on image data which is sequentially outputted from the radiation image detector D when it is positioned at each of the two adjacent positions (for example, the positions Q1 and Q2) and exposed to radiation (hereinafter, two images represented by these image data are referred to as "upper and lower images"), and inputs the information indicating the marker positions to setting error detection unit 83. In order to determine the positions of the markers in each calibration image, a known technique, such as template matching, may be used.

After receiving the information of the marker positions, setting error detection unit 83 detects a setting error of the imaging plane of the radiation image detector D at the two adjacent positions, i.e., the inclination angles $\alpha$ and $\gamma$ and the displacements $\Delta y$ and $\Delta x$, based on the received information. Setting error detection unit inputs information of these setting errors to parameter calculation unit 84. After receiving the information, parameter calculation unit 84 calculates parameters used for image transformation from the inclination angles $\alpha$ and $\gamma$ and displacements $\Delta y$ and $\Delta x$ provided in the information, and inputs the parameters to image correction unit 34.

Basically, ordinary imaging operations, i.e., operations for sequentially imaging adjacent areas N1, N2, - - - of a subject N for providing a combined long length image are performed after the calibration described above. The calibration, however, may be performed, as necessary, in the course of ordinary imaging operations performed on a daily basis. During the ordinary imaging operations, image data sequentially outputted from the radiation image detector D positioned at each of the two adjacent positions (for example, positions Q1 and Q2) and exposed to the radiation are sent to image combining unit 35, where the image data are combined to form a combined image, as described above. But, before that, the image data are subjected, in image correction unit 34, to correction processing to eliminate image distortions arising from the setting errors of the imaging plane based on the parameters described above.

The correction processing is the two-dimensional projective transformation described above. Therefore, each of the parameters is specifically a value of the (3×3) transformation matrix used for the two-dimensional projective transformation. Image combining processing using the corrected image data may prevent misalignment at the joint of a combined image, as described above in detail.

More accurate elimination of image distortion may be achieved by applying shear factors or the like, other than the parameters described above, by way of example. Namely, it is known in the two-dimensional projective transformation that shear transformation may occur depending on ratios of coefficients a, b, c, and d of the (3×3) transformation matrix, and the coefficients a, b, c, and d are called the shear factors. When the two-dimensional projective transformation is carried out using these shear factors to take the shear transformation into account, more reliable elimination of the image distortion due to the setting error of the imaging plane can be achieved. More detailed description of the shear transformation and the shear factors is found in F. Yamaguchi, "GRAPHIC PROCESSING ENGINEERING Through Computer Graphic Display", published by The Nikkan Kogyo Shimbun, Ltd., pp. 73-75, 1981.

In the example described above, the imaging operation is performed to take an image of common markers at each the overlapping areas on radiation image detector D, i.e., the overlapping area of the positions Q1 and Q2, the overlapping of the positions Q2 and Q3, and the overlapping area of the positions Q3 and Q4, and the marker positions are detected each time. However, the imaging may be performed to take the cannon markers at some of the overlapping areas (for example, the overlapping area of the positions Q1 and Q2 and the overlapping area of the positions Q3 and Q4), and only these marker positions may be detected. In this case, the marker positions in the remaining overlapping area (overlapping area of the positions Q2 and Q3 in this example) may be interpolated from the actually detected marker positions.

Further, the inclination angles α and γ and the displacements Δy and Δx with respect to the overlapping area for which the imaging of the marker was not performed can be interpolated from the actually detected marker positions as well as the inclination angles α and γ and the displacements Δy and Δx calculated based on the marker positions. The interpolation may be achieved with any of known methods, such as linear interpolation or spline interpolation.

Figure 19:
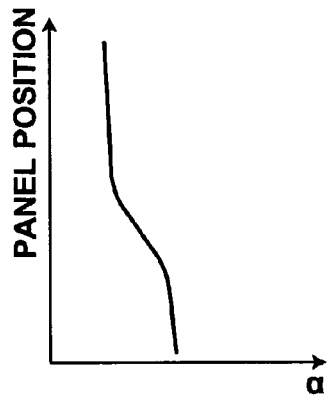
FIG. 19 is a graph illustrating an example relationship between the position of an imaging plane and setting error thereof.

In this case, the inclination angles α and γ and displacements Δy and Δx may vary depending on the shift position (panel position) of the radiation image detector D due to, for example, lack of accuracy of a linear slide mechanism forming shift mechanism 22. FIG. 19 illustrates example characteristics in which, for example, the inclination angle α changes with the panel position. It is, therefore, preferable, when the inclination angle α or the like is obtained through interpolation in the manner as described above, to perform the interpolation by taking into account the characteristics as shown in FIG. 19.

Further, the transformation parameters for correcting image distortion may be obtained from a setting error of the imaging plane, such as the inclination angle α associated with the panel position. The parameters calculated in the manner as described above may be associated with the panel positions and stored in a storage unit in advance, and when a panel position is detected, the stored parameter associated with the panel position may be read out from the storage unit and used for the transformation, instead of calculating transformation parameters each time the transformation operation is performed.

In stead of performing the interpolation described above, several values may be calculated and averaged for a setting error of the imaging plane, such as the inclination angle α, and the averaged value may be used as the setting error of the imaging plane at each of the positions of the radiation image detector D.

Next, a time dependent degradation determination method for a radiation image detector according to an embodiment of the present invention will be described. Radiation image taking apparatus 150 shown in FIG. 18 includes determination control unit 85 constituting a time dependent degradation determination apparatus for a radiation image detector of the present invention. Determination control unit 85 receives imaging plane setting errors, i.e., information of inclination angles α, γ, and deformations Δy, Δx outputted from setting error detection unit 83. The information of these data is obtained each time the calibration described above is performed and inputted to determination control unit 85 where the data are all recorded and retained. In this way, as the time passes, the information of inclination angles α, γ, and deformations Δy, Δx is recorded a plurality of times and retained. The information of each of inclination angles α, γ, and each of deformations Δy, Δx may be obtained by taking an image of a marker together with a subject when an ordinary imaging operation is performed for the subject and from the obtained marker image, other than through the calibration.

Hereinafter, time dependent degradation determination processing for a radiation image detector performed in the present embodiment will be described with reference to the flowchart shown in FIG. 20. First, an ordinary imaging operation is performed (step ST1) and a setting error is detected in setting error detection unit 83 (step ST2). Note that imaging for the aforementioned calibration may be performed instead of the ordinary imaging operation described above. Information of a setting error is inputted to determination control unit 85 each time it is detected and the information is stored in the determination control unit 85 (step ST3). Then, determination control unit 85 analizes a stored log each time information of a new setting error is inputted (step ST4).

Figure 21:
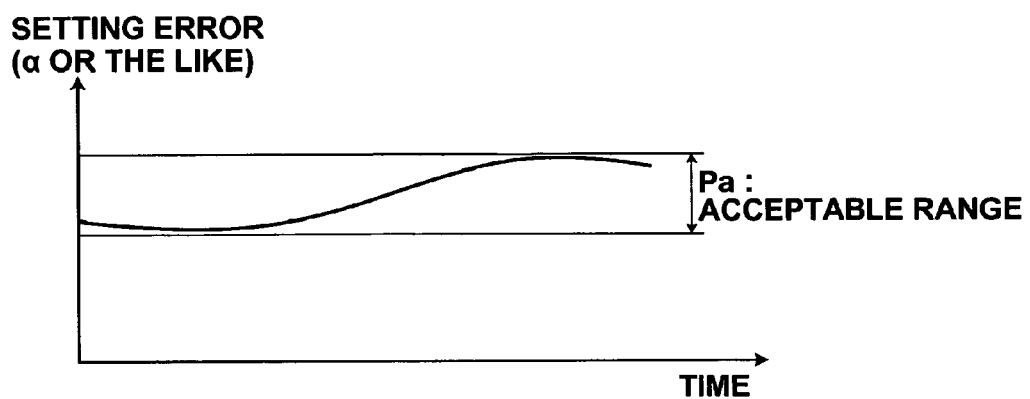
FIG. 21 is a drawing for explaining an example of a first time dependent degradation determination method for a radiation image detector of the present invention.

In the log analysis, a determination is made as to whether or not a plurality of setting error values (with respect to each type of error, such as the inclination angle α) recorded and retained one after another over time falls within a predetermined acceptable range Pa, as illustrated, by way of example, in FIG. 21 (step ST5). If a determination is made that all of the stored setting error values fall within the predetermined acceptable range Pa, determination control unit 85 issues an instruction, to image correction unit 34, to directly perform the aforementioned image correction. Then, the image correction is performed and the image combining processing as described above is performed in image combining unit 35 (step ST6).

In the mean time, if a determination is made in step ST5 that the stored setting errors do not fall within the acceptable range Pa, determination control unit 85 performs processing to notify the user accordingly (step ST7) and issues an instruction, to image correction unit 34, not to perform image correction. This also causes image combining processing, in image combining unit 35, not to be performed. Here, an arrangement may be adopted in which the performance or non-performance of image combining processing is instructed to image combining unit 35 instead of instructing such performance or non-performance of image correction processing.

The processing performed in step ST7 may include, for example, processing for providing notification to maintenance staff, processing for displaying a warning message on the display of console 70, processing for describing in a DICOM (Digital Imaging and Communication in Medicine) tag that the setting error has increased to an unacceptable level. If the processing for describing in the DICOM tag is performed, the described contents are displayed when the tag is displayed in the viewer next time.

The performance of the processing described above allows the user to be notified clearly that the time dependent degradation of the radiation image detector D, i.e., the setting error of the imaging plane has increased to an unacceptable level and an uncontrollably large misalignment due to performance of image correction under such condition to be prevented from occurring at a joint of a combined image.

Figure 22:
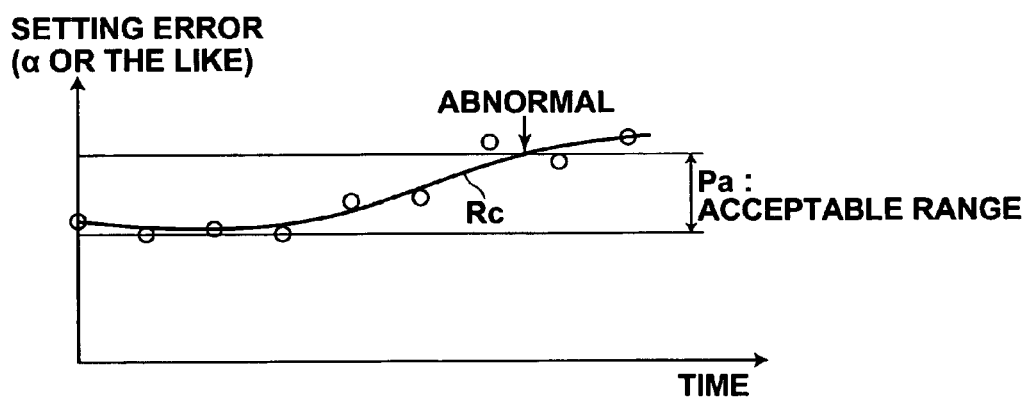
FIG. 22 is a drawing for explaining another example of the first time dependent degradation determination method for a radiation image detector of the present invention.

The determination processing performed in step ST5 may be like that illustrated in FIG. 22, other than that described above. In the example shown in FIG. 21, the fluctuation range of a plurality of setting error values is defined directly from the plurality of setting error values themselves, while in the example shown in FIG. 22, variation charcteristics of a plurality of setting error values are obtained and the fluctuation range of the setting error is defined based on the characteristics. That is, in the present example, when stored setting error values are, for example, like those shown by open circles in FIG. 22, determination control unit 85 obtains, for example, an approximate curve (regression curve) Rc representing the variation charcteristics by a regression analysis method using least-square approach. In the regression analysis method, polynomial approximation by a quadratic function or a cubic function is normally applied.

Figure 20:
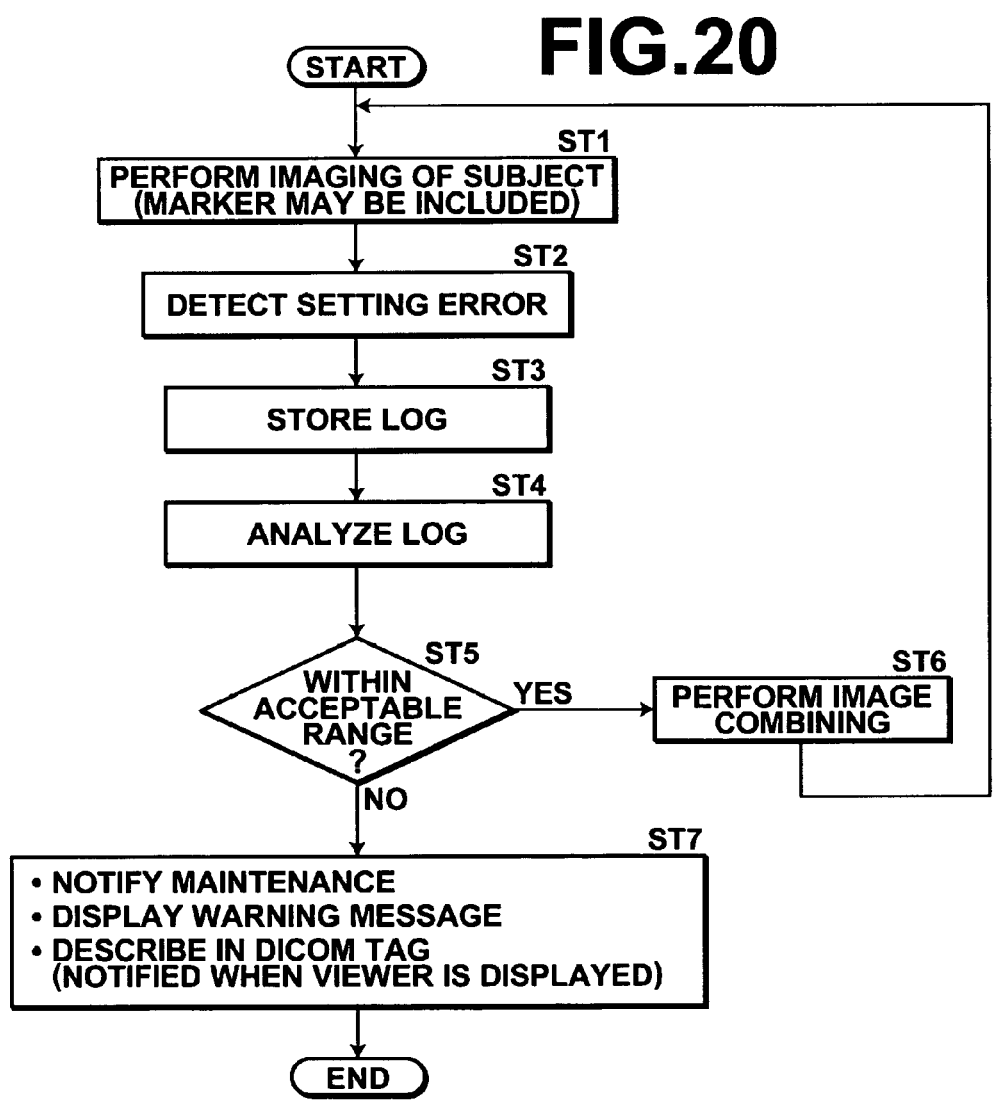
FIG. 20 is a flowchart illustrating a flow of processing performed in a time dependent degradation determination method for a radiation image detector according to an embodiment of the present invention.

Then, determination control unit 85 makes a determination whether or not each possible value of the obtained regression curve falls within the predetermined range Pa (step ST5 of FIG. 20). In the example shown in FIG. 22, a possible value of the regression curver Rc exceeds the predetermined acceptable range Pa at the point denoted by "abnormal". The processing following the judgement result is identical to that of the example shown in FIG. 21, in which the processing of step ST6 of FIG. 20 is performed if each possible value falls withing the predetermined acceptable range Pa and if not, the processing of step ST7 of FIG. 20 is performed. In this way, the present example may provide idential effects to those of the example shown in FIG. 21.

Figure 23:
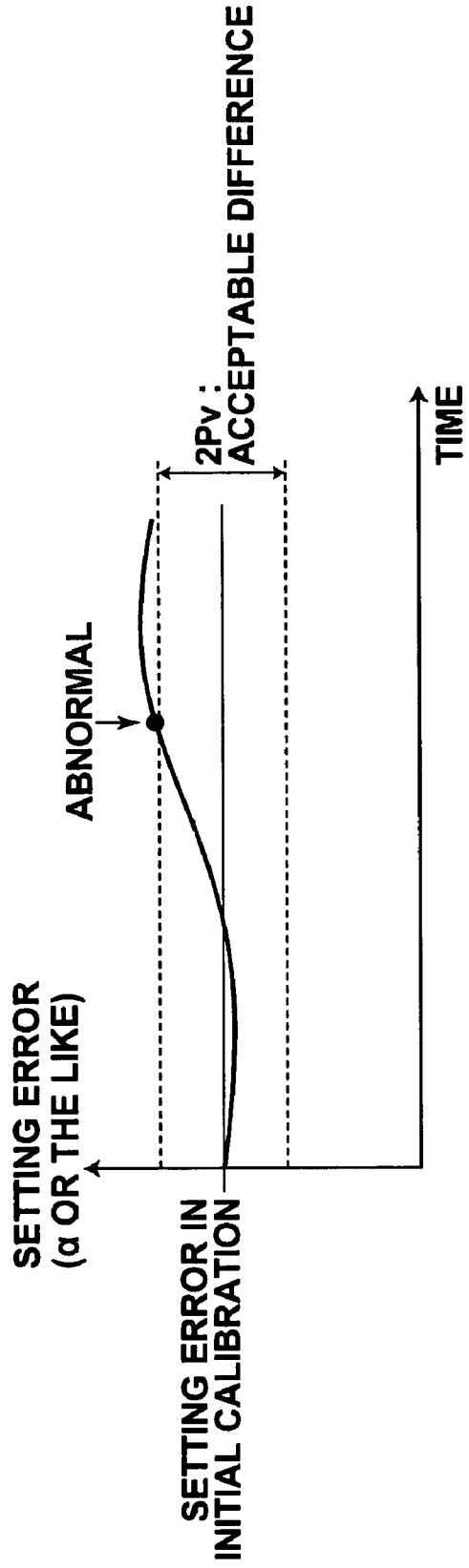
FIG. 23 is a drawing for explaining a second time dependent degradation determination method for a radiation image detector of the present invention.

The determination processing performed in step ST5 may be like that illustrated in FIG. 23, other than those described above. That is, the example shown in FIG. 23 calculates the difference between a setting error value obtained in the initial calibration, i.e., first calibraion and another setting error value of a plurality of those (with respect to each type of error, such as the inclination angle α) recorded and ratianed one after another over time and judges whether or not the difference falls within a predetermined acceptable difference range. The acceptable difference range shown in FIG. 23 extends from the setting error obtained by the initial calibration to plus and minus sides by Pv, totalling 2Pv.

As denoted "abnormal", if the difference between a setting error obtained by the initial calibration and at least one another setting error is greater than a predetermined acceptable difference range, for example, processing identical to that of step ST7 of FIG. 20 is performed. Then, also in this case, the user is notified clearly that the time dependent degradation of the radiation image detector D, i.e., the setting error of the imaging plane has increased to an unacceptable level.

Figure 24:
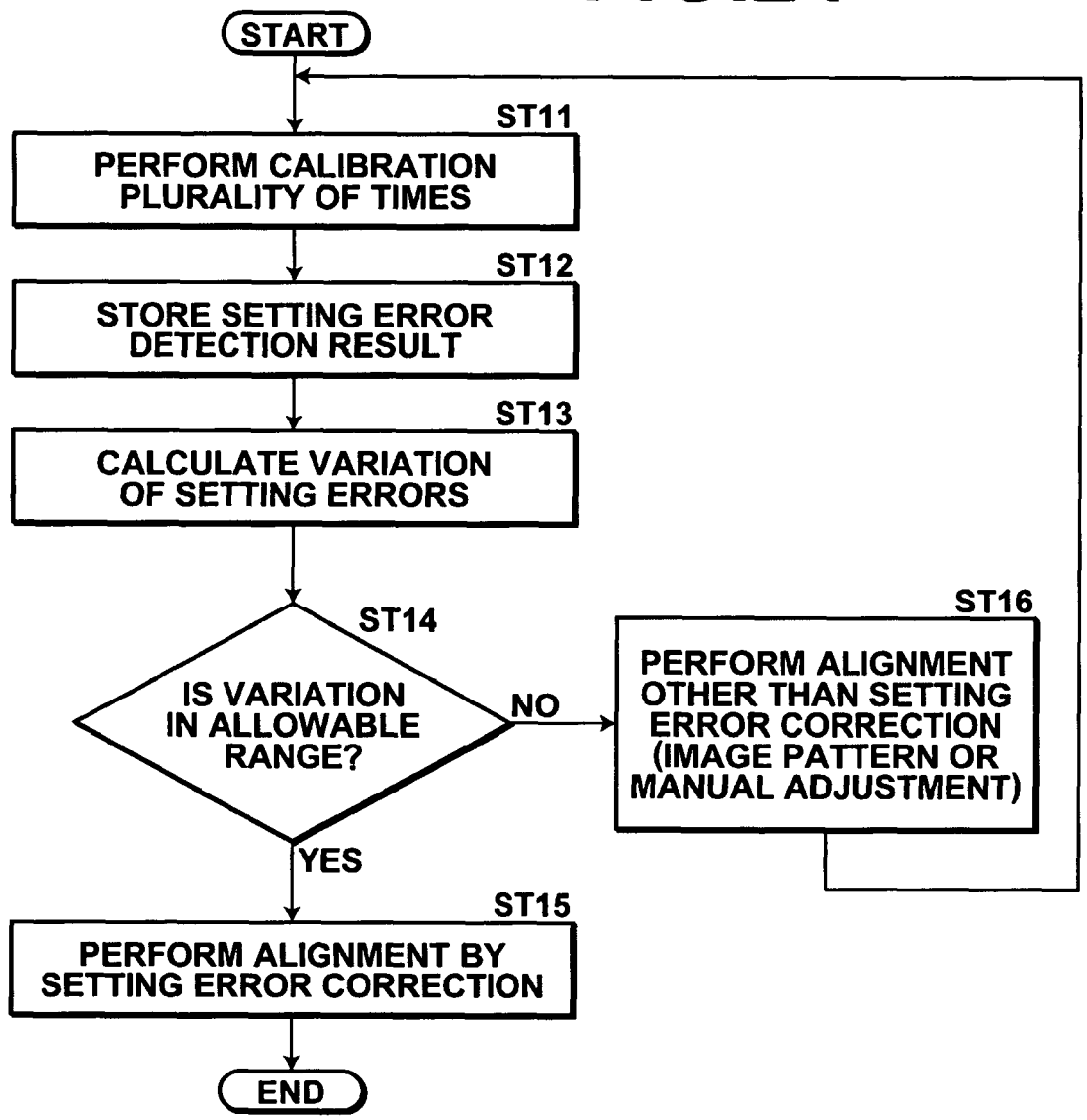
FIG. 24 is a flowchart illustrating a flow of processing performed in a time dependent degradation determination method for a radiation image detector according to another embodiment of the present invention.

Another example of time dependent degradation determination processing for a radiation image detector will now be described with reference to FIG. 24. This processing is also performed using determination control unit 85 shown in FIG. 18 and the like. First, calibration is performed a plurality of times (step ST11) and a setting error detection result is stored for each calibration (step ST12). Then, the variation of the plurality of stored setting errors is calculated (step ST13). This variation also is an index of fluctuation range of setting errors and more specifically, for example, variance may be applied.

Next, a determination is made as to whether or not the variation falls within an acceptable range (step ST14). If the variation falls within an acceptable range, setting error correction, i.e., processing for correcting image distortion arising from the setting error is performed, for example, in image correction unit 34 shown in FIG. 18, and two images to be combined are aligned. On the other hand, if a determination is made in step ST14 that the variation does not fall within the acceptable range, two images to be combined are aligned by a method other than the setting error correction. The method that can be employed other than the setting error correction is, for example, a method of performing the alignment using, for example, an image pattern or a method of performing the alignment by a manual operation.

So far the description has been made of a case in which a radiation image taking apparatus that performs long length imaging in the upright position, but the present invention is also applicable to a radiation image taking apparatus that performs long length imaging in the lateral position.

What is claimed is:

1. A time dependent degradation determination method for a radiation image detector which includes an imaging plane for storing charges by receiving radiation transmitted through a subject according to an amount of radiation received and outputs image data representing radiation image information of the subject through a reading operation, the detector being used to receive radiation transmitted through the same subject each time the detector is shifted and changed in position along a predetermined shift axis, the method comprising the steps of:

detecting a setting error of the imaging plane a plurality of times with the passage of time; and providing, when a fluctuation range of a plurality of setting errors detected exceeds a predetermined acceptable range, an indication or an alarm so indicating.

2. The method of claim 1, wherein, when the radiation image detector is a radiation image detector having an imaging plane with pixels for storing charges disposed in a two-dimensional matrix, an inclination of the matrix with respect to the shift axis is detected as the setting error.

3. The method of claim 2, wherein:

radiation is emitted to the radiation image detector two times by changing the position of the radiation image detector by the shifting so that a common marker is imaged by each radiation emission;

image data representing radiation image information of the marker are obtained by performing the reading operation after each radiation emission; and the inclination is detected based on a positional relationship between each image of the marker represented by image data obtained by each reading operation.

4. The method of claim 1, when the radiation image detector is a radiation image detector having an imaging plane with pixels for storing charges disposed in a two-dimensional matrix, a displacement of the matrix from a predetermined position when receiving radiation is detected as the setting error.

5. The method of claim 4, wherein:

radiation is emitted to the radiation image detector two times by changing the position of the radiation image detector by the shifting so that a common marker is imaged by each radiation emission;

image data representing radiation image information of the marker are obtained by performing the reading operation after each radiation emission; and the displacement is detected based on a positional relationship between each image of the marker represented by image data obtained by each reading operation.

6. The method of claim 1, wherein, when combining image data outputted from the radiation image detector that received radiation transmitted through the same subject each time the detector was shifted and changed in position along the predetermined shift axis, the image data representing the subject with respect to each position, correction processing for eliminating an image distortion arising from the setting error is performed on at least a portion of the image data prior to combining the image data, while the correction processing is not performed if a situation arises in which the indication or the alarm needs to be provided.

7. A time dependent degradation determination method for a radiation image detector which includes an imaging plane for storing charges by receiving radiation transmitted through a subject according to an amount of radiation received and outputs image data representing radiation image information of the subject through a reading operation, the detector being used to receive radiation transmitted through the same subject each time the detector is shifted and changed in position along a predetermined shift axis, the method comprising the steps of:
  detecting a setting error of the imaging plane a plurality of times with the passage of time; and
  providing, when a difference between a setting error detected first and at least one another setting error subsequently detected exceeds a predetermined acceptable difference, an indication or an alarm so indicating.

8. The method of claim 7, wherein, when the radiation image detector is a radiation image detector having an imaging plane with pixels for storing charges disposed in a two-dimensional matrix, an inclination of the matrix with respect to the shift axis is detected as the setting error.

9. The method of claim 8, wherein:
  radiation is emitted to the radiation image detector two times by changing the position of the radiation image detector by the shifting so that a common marker is imaged by each radiation emission;
  image data representing radiation image information of the marker are obtained by performing the reading operation after each radiation emission; and
  the inclination is detected based on a positional relationship between each image of the marker represented by image data obtained by each reading operation.

10. The method of claim 7, when the radiation image detector is a radiation image detector having an imaging plane with pixels for storing charges disposed in a two-dimensional matrix, a displacement of the matrix from a predetermined position when receiving radiation is detected as the setting error.

11. The method of claim 10, wherein:
  radiation is emitted to the radiation image detector two times by changing the position of the radiation image detector by the shifting so that a common marker is imaged by each radiation emission;
  image data representing radiation image information of the marker are obtained by performing the reading operation after each radiation emission; and
  the displacement is detected based on a positional relationship between each image of the marker represented by image data obtained by each reading operation.

12. An apparatus for implementing a time dependent degradation determination method for a radiation image detector which includes an imaging plane for storing charges by receiving radiation transmitted through a subject according to an amount of radiation received and outputs image data representing radiation image information of the subject through a reading operation, the detector being used to receive radiation transmitted through the same subject each time the detector is shifted and changed in position along a predetermined shift axis, the method comprising the steps of:
  detecting a setting error of the imaging plane a plurality of times with the passage of time; and
  providing, when a fluctuation range of a plurality of setting errors detected exceeds a predetermined acceptable range, an indication or an alarm so indicating,
  wherein the apparatus comprises:
  a means for detecting a setting error of the imaging plane a plurality of times with the passage of time;
  a means for storing a plurality of setting errors detected; and
  a means for providing, when a fluctuation range of a plurality of setting errors stored exceeds a predetermined acceptable range, an indication or an alarm so indicating.

13. An apparatus for implementing a time dependent degradation determination method for a radiation image detector which includes an imaging plane for storing charges by receiving radiation transmitted through a subject according to an amount of radiation received and outputs image data representing radiation image information of the subject through a reading operation, the detector being used to receive radiation transmitted through the same subject each time the detector is shifted and changed in position along a predetermined shift axis, the method comprising the steps of:
  detecting a setting error of the imaging plane a plurality of times with the passage of time; and
  providing, when a difference between a setting error detected first and at least one another setting error subsequently detected exceeds a predetermined acceptable difference, an indication or an alarm so indicating,
  wherein the apparatus comprises:
  a means for detecting a setting error of the imaging plane a plurality of times with the passage of time;
  a means for storing a plurality of setting errors detected; and
  a means for providing, when a difference between a setting error detected first of a plurality of setting errors stored and at least one another setting error subsequently detected exceeds a predetermined acceptable difference, an indication or an alarm so indicating.

14. An apparatus for implementing a time dependent degradation determination method for a radiation image detector which includes an imaging plane for storing charges by receiving radiation transmitted through a subject according to an amount of radiation received and outputs image data representing radiation image information of the subject through a reading operation, the detector being used to receive radiation transmitted through the same subject each time the detector is shifted and changed in position along a predetermined shift axis, the method comprising the steps of:
  detecting a setting error of the imaging plane a plurality of times with the passage of time; and
  providing, when a difference between a setting error detected first and at least one another setting error subsequently detected exceeds a predetermined acceptable difference, an indication or an alarm so indicating,
  wherein, when the radiation image detector is a radiation image detector having an imaging plane with pixels for storing charges disposed in a two-dimensional matrix, an inclination of the matrix with respect to the shift axis is detected as the setting error,
  wherein:
  radiation is emitted to the radiation image detector two times by changing the position of the radiation image detector by the shifting so that a common marker is imaged by each radiation emission;

image data representing radiation image information of the marker are obtained by performing the reading operation after each radiation emission; and the inclination is detected based on a positional relationship between each image of the marker represented by image data obtained by each reading operation, wherein the apparatus comprises:

a radiation emission means for emitting radiation, through the common marker, to the radiation image detector;

a shifting means for shifting the radiation image detector in the shift axis direction;

a means for obtaining image data from the radiation image detector each time the shifting and radiation emission are performed; and a calculation means for calculating the inclination based on a positional relationship between each image of the marker represented by the image data obtained.

15. An apparatus for implementing a time dependent degradation determination method for a radiation image detector which includes an imaging plane for storing charges by receiving radiation transmitted through a subject according to an amount of radiation received and outputs image data representing radiation image information of the subject through a reading operation, the detector being used to receive radiation transmitted through the same subject each time the detector is shifted and changed in position along a predetermined shift axis, the method comprising the steps of:

detecting a setting error of the imaging plane a plurality of times with the passage of time; and providing, when a difference between a setting error detected first and at least one another setting error subsequently detected exceeds a predetermined acceptable difference, an indication or an alarm so indicating, wherein, when the radiation image detector is a radiation image detector having an imaging plane with pixels for storing charges disposed in a two-dimensional matrix, an inclination of the matrix with respect to the shift axis is detected as the setting error, wherein:

radiation is emitted to the radiation image detector two times by changing the position of the radiation image detector by the shifting so that a common marker is imaged by each radiation emission;

image data representing radiation image information of the marker are obtained by performing the reading operation after each radiation emission; and the inclination is detected based on a positional relationship between each image of the marker represented by image data obtained by each reading operation, wherein the apparatus comprises:

a radiation emission means for emitting radiation, through the common marker, to the radiation image detector;

a shifting means for shifting the radiation image detector in the shift axis direction;

a means for obtaining image data from the radiation image detector each time the shifting and radiation emission are performed; and a calculation means for calculating the inclination based on a positional relationship between each image of the marker represented by the image data obtained.

16. An apparatus for implementing a time dependent degradation determination method for a radiation image detector which includes an imaging plane for storing charges by receiving radiation transmitted through a subject according to an amount of radiation received and outputs image data representing radiation image information of the subject through a reading operation, the detector being used to receive radiation transmitted through the same subject each time the detector is shifted and changed in position along a predetermined shift axis, the method comprising the steps of:

detecting a setting error of the imaging plane a plurality of times with the passage of time; and providing, when a fluctuation range of a plurality of setting errors detected exceeds a predetermined acceptable range, an indication or an alarm so indicating when the radiation image detector is a radiation image detector having an imaging plane with pixels for storing charges disposed in a two-dimensional matrix, a displacement of the matrix from a predetermined position when receiving radiation is detected as the setting error, wherein:

radiation is emitted to the radiation image detector two times by changing the position of the radiation image detector by the shifting so that a common marker is image data representing radiation image information of the marker are obtained by performing the reading operation after each radiation emission; and the displacement is detected based on a positional relationship between each image of the marker represented by image data obtained by each reading operation, wherein the apparatus comprises:

a radiation emission means for emitting radiation, through the common marker, to the radiation image detector;

a shifting means for shifting the radiation image detector in the shift axis direction;

a means for obtaining image data from the radiation image detector each time the shifting and radiation emission are performed; and a calculation means for calculating the displacement based on a positional relationship between each image of the marker represented by the image data obtained.

17. An apparatus for implementing a time dependent degradation determination method for a radiation image detector which includes an imaging plane for storing charges by receiving radiation transmitted through a subject according to an amount of radiation received and outputs image data representing radiation image information of the subject through a reading operation, the detector being used to receive radiation transmitted through the same subject each time the detector is shifted and changed in position along a predetermined shift axis, the method comprising the steps of:

detecting a setting error of the imaging plane a plurality of times with the passage of time; and providing, when a difference between a setting error detected first and at least one another setting error subsequently detected exceeds a predetermined acceptable difference, an indication or an alarm so indicating, when the radiation image detector is a radiation image detector having an imaging plane with pixels for storing charges disposed in a two-dimensional matrix, a displacement of the matrix from a predetermined position when receiving radiation is detected as the setting error, wherein:

radiation is emitted to the radiation image detector two times by changing the position of the radiation image detector by the shifting so that a common marker is imaged by each radiation emission;

image data representing radiation image information of the marker are the displacement is detected based on a positional relationship between each image of the marker represented by image data obtained by each reading operation wherein the apparatus comprises:

a radiation emission means for emitting radiation, through the common marker, to the radiation image detector;

a shifting means for shifting the radiation image detector in the shift axis direction;

a means for obtaining image data from the radiation image detector each time the shifting and radiation emission are performed; and a calculation means for calculating the displacement based on a positional relationship between each image of the marker represented by the image data obtained.

* * * * *